(12) United States Patent
Berek et al.

(10) Patent No.: US 10,267,802 B2
(45) Date of Patent: Apr. 23, 2019

(54) METHODS OF PROGNOSIS AND DIAGNOSIS OF OVARIAN CANCER

(71) Applicant: The Board of Trustees of the Leland Stanford Junior University, Stanford, CA (US)

(72) Inventors: Jonathan Berek, Stanford, CA (US); Wendy Fantl, San Francisco, CA (US); Veronica Gonzalez, Stanford, CA (US); Garry P. Nolan, San Francisco, CA (US); Nikolay Samusik, Palo Alto, CA (US)

(73) Assignee: The Board of Trustees of the Leland Stanford Junior University, Standord, CA (US)

( * ) Notice: Subject to any disclaimer, the term of this patent is extended or adjusted under 35 U.S.C. 154(b) by 0 days.

(21) Appl. No.: 15/275,043

(22) Filed: Sep. 23, 2016

(65) Prior Publication Data

US 2017/0082628 A1    Mar. 23, 2017

Related U.S. Application Data

(60) Provisional application No. 62/222,417, filed on Sep. 23, 2015.

(51) Int. Cl.
*G01N 33/574* (2006.01)

(52) U.S. Cl.
CPC ......... *G01N 33/57449* (2013.01); *G01N 2333/4703* (2013.01); *G01N 2800/52* (2013.01); *G01N 2800/54* (2013.01)

(58) Field of Classification Search
CPC .................................................. G01N 33/574
USPC ...................................................... 424/133.1
See application file for complete search history.

(56) References Cited

U.S. PATENT DOCUMENTS

| 7,504,225 | B2 | 3/2009 | Ring et al. |
| 7,550,256 | B2 | 6/2009 | Georges et al. |
| 2007/0286865 | A1 | 12/2007 | Moore et al. |
| 2013/0224772 | A1* | 8/2013 | Hellstrom ........ G01N 33/57449 435/7.92 |
| 2013/0267439 | A1 | 10/2013 | Mansfield et al. |
| 2015/0322530 | A1 | 11/2015 | Orsulic et al. |

FOREIGN PATENT DOCUMENTS

| WO | 2014138183 A1 | 9/2014 |
| WO | 2014182896 A1 | 11/2014 |

OTHER PUBLICATIONS

Shah et al. (Cancer Letters, 2011, 311: 66-76).*
Issadore et al. (Sci Transl Med. Jul. 4, 2012; 4(141): 141ra92).*
Cancer Genome Atlas Research Network (2011) Integrated genomic analyses of ovarian carcinoma. Nature 474:609-615.
Konecny et al. (2014) Prognostic and therapeutic relevance of molecular subtypes in high-grade serous ovarian cancer. J. Natl. Cancer Inst. 106.
Patch et al. (2015) Whole-genome characterization of chemoresistant ovarian cancer. Nature 521:489-494.
Tothill et al. (2008) Novel molecular subtypes of serous and endometrioid ovarian cancer linked to clinical outcome. Clin. Cancer Res. 14:5198-5208.
Leung et al. (2014) Ovarian cancer biomarkers: current state and future implications from high-throughput technologies. Adv. Clin. Chem. 66:25-77.
Montagnana et al. (2011) HE4 in ovarian cancer: from discovery to clinical application. Adv. Clin. Chem. 55:1-20.
Liu et al. (2014) New strategies in ovarian cancer: translating the molecular complexity of ovarian cancer into treatment advances. Clin. Cancer Res. 20:5150-5156.
Bowtell et al. (2015) Rethinking ovarian cancer II: reducing mortality from high-grade serous ovarian cancer. Nat. Rev. Cancer 15:668-679.
Davidson et al. (2012) Epithelial-mesenchymal transition in ovarian carcinoma. Front Oncol. 2:33.
Nieto (2013) Epithelial plasticity: a common theme in embryonic and cancer cells. Science 342:1234850.
Davidowitz et al. (2014) Mesenchymal gene program-expressing ovarian cancer spheroids exhibit enhanced mesothelial clearance. J. Clin. Invest. 124:2611-2625.
Stewart et al. (2011) Phenotypic heterogeneity and instability of human ovarian tumor-initiating cells. Proc. Natl. Acad. Sci. U.S.A. 108:6468-6473.
Zhang et al. (2014) Ovarian cancer stem cells express ROR1, which can be targeted for anti-cancer-stem-cell therapy. Proc. Natl. Acad. Sci. U.S.A. 111:17266-17271.
Lu et al. (2012) Human epididymis protein 4 (HE4) plays a key role in ovarian cancer cell adhesion and motility. Biochem. Biophys. Res. Commun. 419:274-280.
Gabay et al. (2014) MYC activation is a hallmark of cancer initiation and maintenance. Cold Spring Harb Perspect Med 4.
Lawson et al. (2015) Single-cell analysis reveals a stem-cell program in human metastatic breast cancer cells. Nature 526:131-135.
Gitsch et al. (1991) Immunohistochemical differentiation between ovarian granulosa cell tumors and ovarian carcinomas Arch. Gynecol. Obstet. 249:173-177.

* cited by examiner

*Primary Examiner* — Yan Xiao
(74) *Attorney, Agent, or Firm* — Jenny L. Buchbinder; Bozicevic, Field & Francis LLP

(57) ABSTRACT

Cellular markers indicating a poor prognosis for ovarian cancer patients are disclosed. In particular, the invention relates to methods utilizing the frequency of a subset of cells in ovarian tumor tissue expressing vimentin, cMyc, or HE4, or any combination thereof, to predict an ovarian cancer patient will relapse.

15 Claims, 15 Drawing Sheets

METHODS OF PROGNOSIS AND DIAGNOSIS OF OVARIAN CANCER

STATEMENT REGARDING FEDERALLY SPONSORED RESEARCH OR DEVELOPMENT

This invention was made with Government support under contract W81XWH-12-1-0591 awarded by the Department of Defense. The Government has certain rights in the invention.

TECHNICAL FIELD

The present invention pertains generally to methods for prognosis and diagnosis of ovarian cancer. In particular, the invention relates to a method utilizing the frequency of ovarian cells expressing vimentin, cMyc, or human epididymis protein 4 (HE4), or any combination thereof, to predict whether an ovarian cancer patient will relapse.

BACKGROUND

Ovarian cancer is the most lethal gynecologic malignancy and the fifth leading cause of death in women. Women with ovarian cancer are typically diagnosed at late stage, when the cancer has spread into the peritoneal cavity and surgical removal is very challenging and incomplete. Five year survival for these late-stage patients is around 30% with recurrent chemotherapy-resistant disease accounting for most ovarian cancer deaths. This contrasts with a 5-year overall survival time of 90% for patients with early-stage disease (Bast et al. (2011) Ann. Oncol. 22 Suppl 8:viii5-viii15; Landen et al. (2008) J. Clin. Oncol. 26:995-1005; Vaughan et al. (2011) Nat. Rev. Cancer 11:719-725). A subset of about 25% of ovarian cancer patients harbor mutations in the BRCA1 or BRCA2 cancer-predisposition genes (Alsop et al. (2012) J. Clin. Oncol. 30:2654-2663; Clamp et al. (2015) Lancet Oncol. 16(1):10-12; Hennessy et al. (2010) J. Clin. Oncol. 28:3570-3576). These patients generally have a more favorable response to chemotherapy and are also candidates for poly-ADP-ribose polymerase (PARP) inhibitors (Clamp et al., supra; Ashworth et al. (2008) J. Clin. Oncol. 26:3785-3790; Sonnenblick et al. (2015) Nat. Rev. Clin. Oncol. 12:27-41; Underhill et al. (2011) Ann. Oncol. 22:268-279; Ledermann et al. (2014) Lancet Oncol. 15:852-861; Oza et al. (2014) Lancet Oncol. 15(11):1207-1214). As such sequencing a buccal wash or blood sample from patients is a companion diagnostic for deciding whether or not a patient will receive a PARP inhibitor as part of their therapeutic regiment (Gunderson et al. (2015) Expert Rev. Mol. Diagn. 15:1111-1116). However, from numerous genomic studies, extensive intra- and inter-tumoral heterogeneity has been documented in both BRCA and non-BRCA ovarian tumors (Cancer Genome Atlas Research Network (2011) Nature 474:609-615; Konecny et al. (2014) J. Natl. Cancer Inst. 106; Patch et al. (2015) Nature 521:489-494; Tothill et al. (2008) Clin. Cancer Res. 14:5198-5208). To date little of the genomic information has been incorporated into clinical decision-making regarding disease management. At present several FDA-approved markers are available for monitoring various aspects of ovarian cancer. For many decades serum levels of MUC16, measured by CA125 antibody, have been used to monitor treatment and disease recurrence. However, over the past 5 years, new tests have been FDA-approved to monitor ovarian cancer treatment and disease recurrence, including serum levels of human epididymis protein (HE4). However, results from several studies report variable values for specificity and sensitivity. In particular, CA125 has typically poor specificity (Leung et al. (2014) Adv. Clin. Chem. 66:25-77). In summary, these tests, while of some clinical utility, can be unreliable.

Therefore, identification of reliable biomarkers for early ovarian cancer detection, monitoring treatment, as well as for predicting time to relapse is urgently needed to improve survival rates.

SUMMARY

The present invention is based on the discovery that the frequency of ovarian cells expressing vimentin, cMyc, of HE4, or any combination thereof, can be used to predict whether an ovarian cancer patient will relapse.

In one aspect, the invention includes a prognostic method for predicting relapse of an ovarian cancer patient and treating the patient for ovarian cancer, the method comprising: a) obtaining a sample of ovarian tumor tissue or cells from the patient; b) measuring frequency of cells expressing one or more markers selected from the group consisting of vimentin, cMyc and HE4 in the sample; and c) comparing the frequency of cells expressing said markers in the sample to respective reference value ranges for said markers for ovarian cancer patients who do not relapse, wherein increased frequency of the one or more markers selected from the group consisting of vimentin, cMyc and HE4 compared to the reference value ranges for said markers for ovarian cancer patients who do not relapse indicates the patient will relapse within 1 year; and d) treating the patient with surgery, radiation therapy, chemotherapy, targeted therapy, anti-angiogenic therapy, or immunotherapy, or any combination thereof if the patient is predicted to relapse. Thus, increased frequency of cells positive for vimentin and HE4, cells positive for vimentin and cMyc, cells positive for HE4 and cMyc, or cells positive for vimentin, HE4, and cMyc compared to the reference value ranges for ovarian cancer patients who do not relapse indicates increased likelihood that the ovarian cancer patient will relapse. In addition, increased frequency of cells positive for vimentin and having higher levels of expression of cMyc and HE4 compared to the cells in the control sample further indicates increased likelihood that the ovarian cancer patient will relapse. The ovarian cancer patient is predicted to relapse if the frequency of cells positive for one or more of the markers selected from the group consisting of vimentin, cMyc and HE4 is greater than 1%.

In another embodiment, the method further comprises detecting whether the cells, having increased frequency of one or more markers selected from the group consisting of vimentin, cMyc and HE4, are E-cadherin negative cells, wherein absence of the E-cadherin in the cells indicates increased likelihood that the ovarian cancer patient will relapse compared to if the cells are E-cadherin positive.

In another embodiment, the sample obtained from the patient is an ovarian tumor sample, such as from a biopsy or surgical resection. In another embodiment, the ovarian cancer is high-grade serous ovarian cancer.

The markers can be detected by any suitable method, including, but not limited to, mass cytometry, flow cytometry, immunohistochemistry, immunofluorescence, or multiplexed ion beam imaging (MIBI) or other multi-parametric single cell analysis technology. In certain embodiments, detecting the markers comprises using an antibody that specifically binds to vimentin, cMyc or HE4, or a fragment thereof containing an antigenic determinant of vimentin, cMyc or HE4. The antibody may be a monoclonal antibody, a polyclonal antibody, a chimeric antibody, a recombinant fragment of an antibody, an Fab fragment, an Fab' fragment, an $F(ab')_2$ fragment, an $F_v$ fragment, or an $scF_v$ fragment. The antibody may be conjugated to a detectable label to facilitate detection of the marker. Exemplary labels include a stable-metal isotope or a fluorescent label.

In another embodiment, measuring the frequency of cells expressing one or more of the vimentin, cMyc, or HE4 markers comprises detecting the markers on single cells.

An ovarian cancer patient who is predicted to relapse by the methods described herein may be treated for ovarian cancer in a variety of ways known in the art. For example, treatment by surgery may comprise a unilateral oophorectomy, a bilateral oophorectomy, or a salpingo oophorectomy. Treatment by chemotherapy may comprise administering, for example, a platinum or a nonplatinum chemotherapeutic agent or a combination thereof. Exemplary chemotherapeutic agents for treatment of ovarian cancer include paclitaxel, cisplatin, topotecan, doxorubicin, epirubicin, and gemcitabine, docetaxel, carboplatin, and taxol. In one embodiment, chemotherapy comprises administering a platinum chemotherapeutic agent and taxol. Treatment by immunotherapy may comprise administering, for example, an immune-modulatory agent selected from the group consisting of an anti-PD1 agent, an anti-PDL1 agent, and an anti-CTLA4 agent. Treatment by targeted therapy may comprise administering, for example, a poly-(ADP)-ribose polymerase (PARP) inhibitor, a PI3 kinase inhibitor, or a targeted bromodomain and extra-terminal (BET) family inhibitor. Treatment by anti-angiogenic therapy may comprise administering a vascular endothelial growth factor (VEGF) inhibitor, a tyrosine kinase inhibitor (TKI), or an EphA2 inhibitor. In one embodiment the VEGF inhibitor is bevacizumab.

In another aspect, the invention includes a method of monitoring the efficacy of a therapy for treating ovarian cancer in a patient, the method comprising: measuring frequency of cells expressing one or more markers selected from the group consisting of vimentin, cMyc and HE4 in a first sample of ovarian tumor tissue or cells derived from the patient before the patient undergoes said therapy and a second sample of ovarian tumor tissue or cells derived from the patient after the patient undergoes the therapy, wherein increased frequency of cells expressing the one or more markers selected from the group consisting of vimentin, cMyc and HE4 in the second sample compared to the frequency of cells expressing the markers in the first sample indicates that the patient is worsening, and decreased frequency of cells expressing the one or more markers selected from the group consisting of vimentin, cMyc and HE4 in the second sample compared to the frequency of cells expressing the markers in the first sample indicates that the patient is improving. For example, increased frequency of cells positive for vimentin and HE4, cells positive for vimentin and cMyc, cells positive for HE4 and cMyc, or cells positive for vimentin, HE4, and cMyc in the second sample compared to their frequency in the first sample indicates that the patient is worsening.

In certain embodiments, the method further comprises detecting whether the cells having increased frequency of the one or more markers selected from the group consisting of vimentin, cMyc and HE4 are E-cadherin negative cells, wherein absence of the E-cadherin in the cells indicates increased likelihood that the ovarian cancer patient will relapse compared to if the cells are E-cadherin positive.

In another aspect, the invention includes a kit for predicting whether an ovarian cancer patient will relapse comprising at least one agent for detecting cells expressing one or more markers selected from the group consisting of vimentin, cMyc, and HE4. In certain embodiments, at least one agent is an antibody selected from the group consisting of an antibody that specifically binds to vimentin, an antibody that specifically binds to cMyc, and an antibody that specifically binds to HE4. The antibody may be conjugated to a detectable label such as a metal isotope or fluorescent label. In one embodiment, the kit comprises a set of antibodies comprising an antibody that specifically binds to vimentin, an antibody that specifically binds to cMyc, and an antibody that specifically binds to HE4, wherein each antibody is conjugated to a metal isotope suitable for performing mass cytometry or multiplexed ion beam imaging (MIBI).

In another aspect, the invention includes a system for predicting whether an ovarian cancer patient will relapse, the system comprising: a) a set of antibodies comprising an antibody that specifically binds to vimentin, an antibody that specifically binds to cMyc, and an antibody that specifically binds to HE4, wherein each antibody is conjugated to a detectable label; and b) a computer model or algorithm for analyzing the frequency of cells expressing one or more markers selected from the group consisting of the vimentin, cMyc, or HE4 in a sample of ovarian tissue or cells from a patient. In certain embodiments, such a system is included in a kit for predicting whether an ovarian cancer patient will relapse.

These and other embodiments of the patient invention will readily occur to those of skill in the art in view of the disclosure herein.

The colour keys represent the median ar sin h-transformed protein expression (Methods). Dark gray represents a signal <1.0 in raw mass cytometry counts with the rest of the gray-scale assigned to increasing quantiles of positive signal >1.0 in raw mass cytometry counts).

Figure 3A:
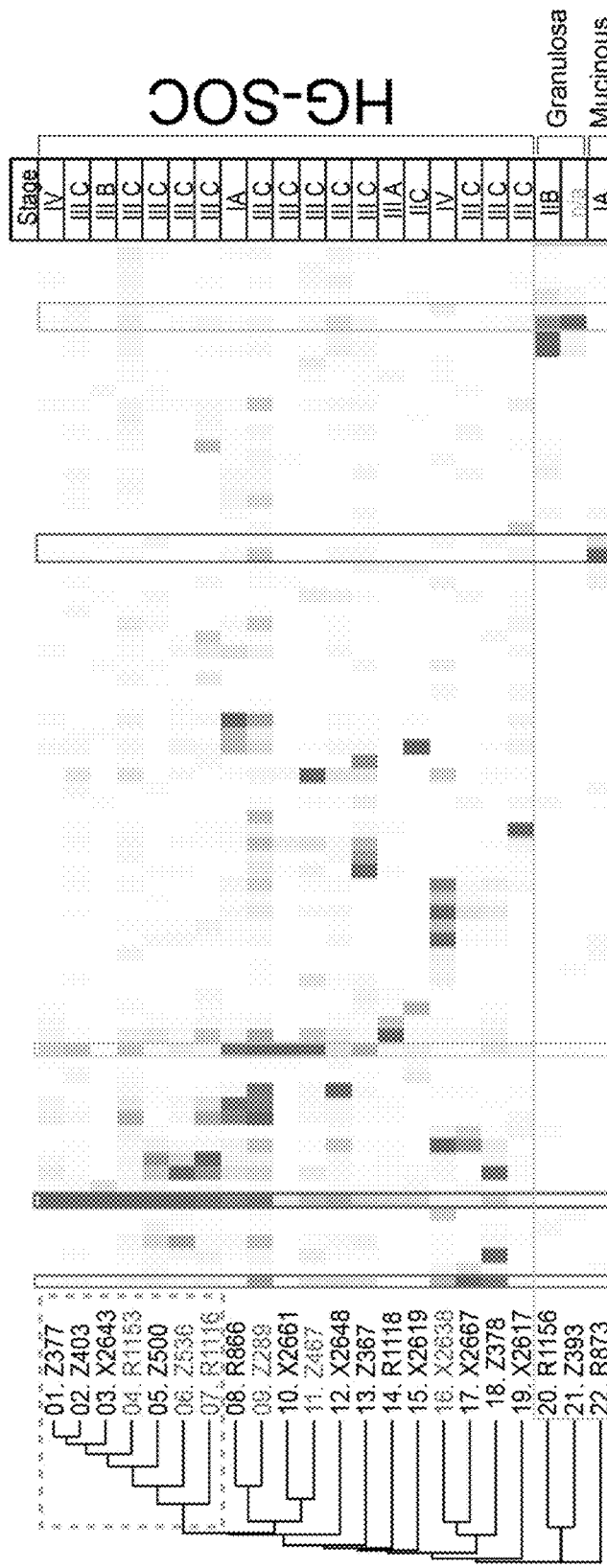
Figure 3B:
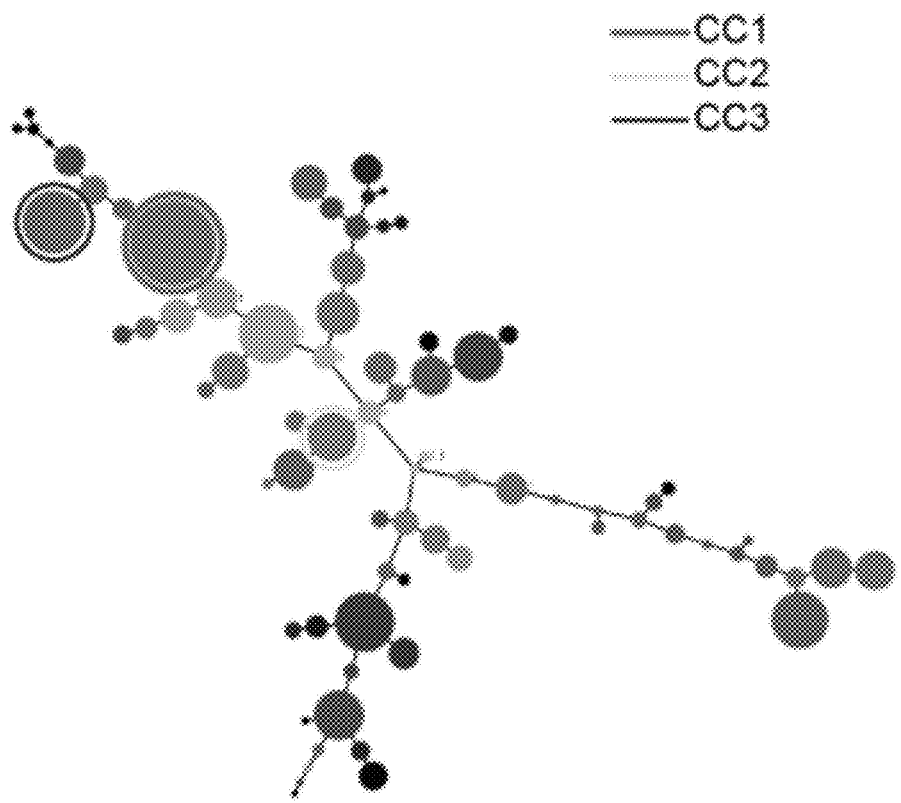
Figure 3C:
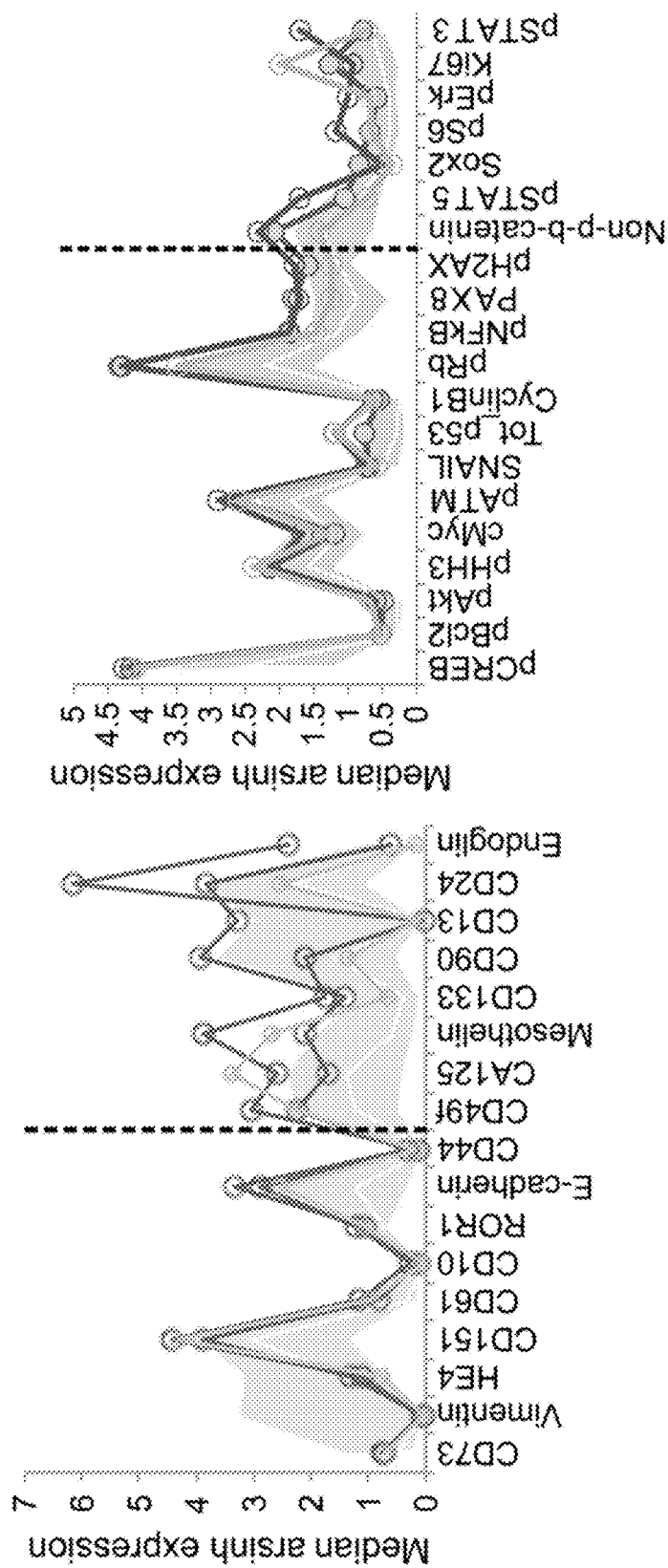

FIGS. 3A-3C show grouped samples based on cell population frequencies. FIG. 3A shows a heat-map with a dendrogram (left-hand side) depicting cell frequency distribution within clusters for individual tumors (n=22). Three cell clusters (common clusters (CCs)) with the highest median frequency across the HG-SOC samples are depicted with vertical boxes (CC1, CC2, and CC3). FIG. 3B shows the positions of common clusters (CC) on a composite MST. FIG. 3C shows median protein expression in CC1, 2 and 3

(ar sin h-transformed raw median counts). Surface proteins, used to cluster cells, are indicated in the left-hand plot and intracellular proteins are indicated in the right-hand plot. Vertical dashed lines set a boundary between conserved and variably expressed proteins within the three clusters. Median protein expression for all other clusters (white line) and the interquartile range (solid grey area) is shown.

Figure 4A:
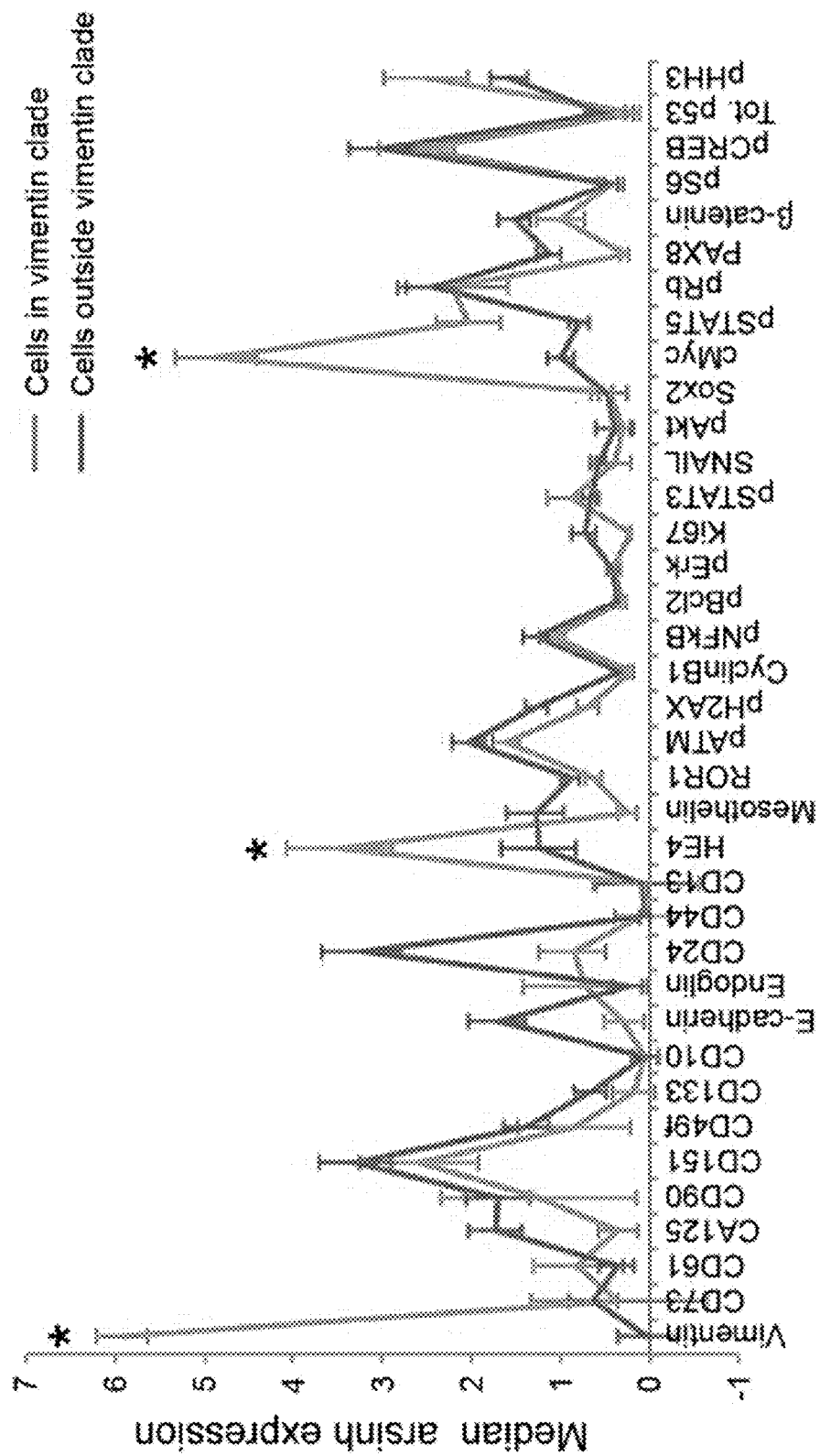
Figure 4B:
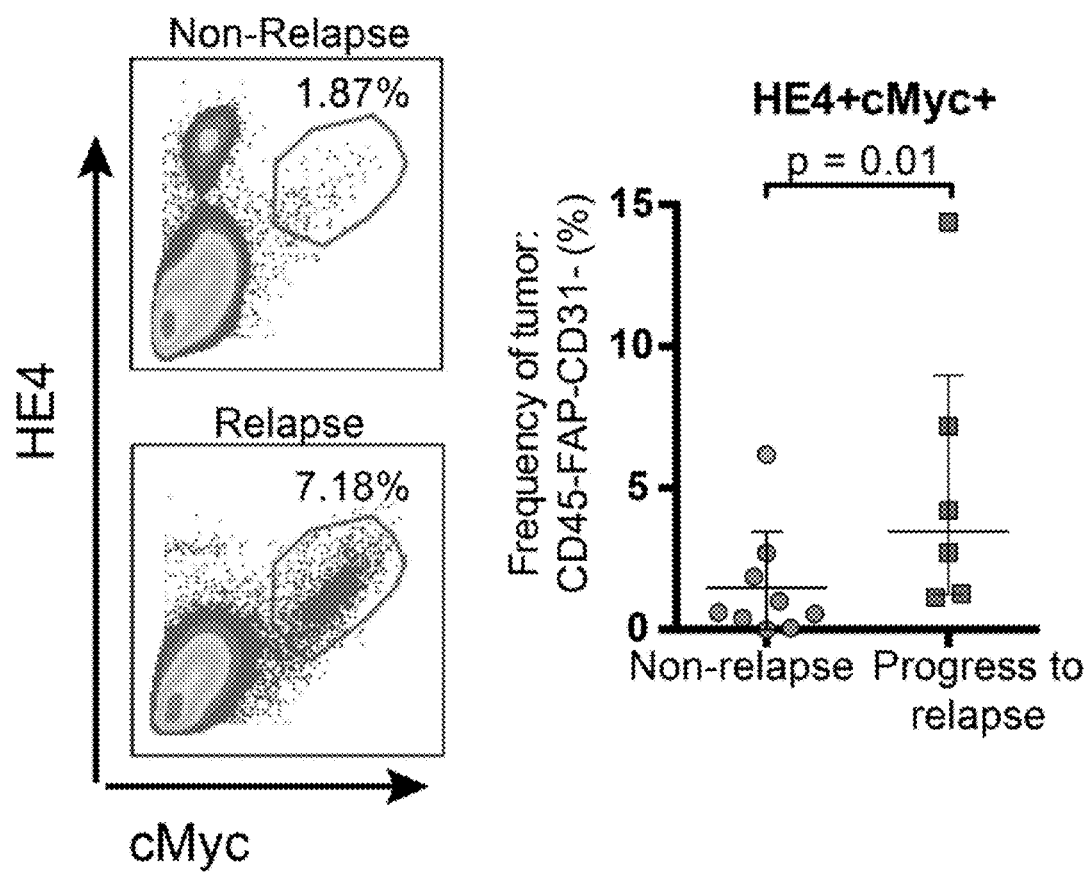
Figure 4C:
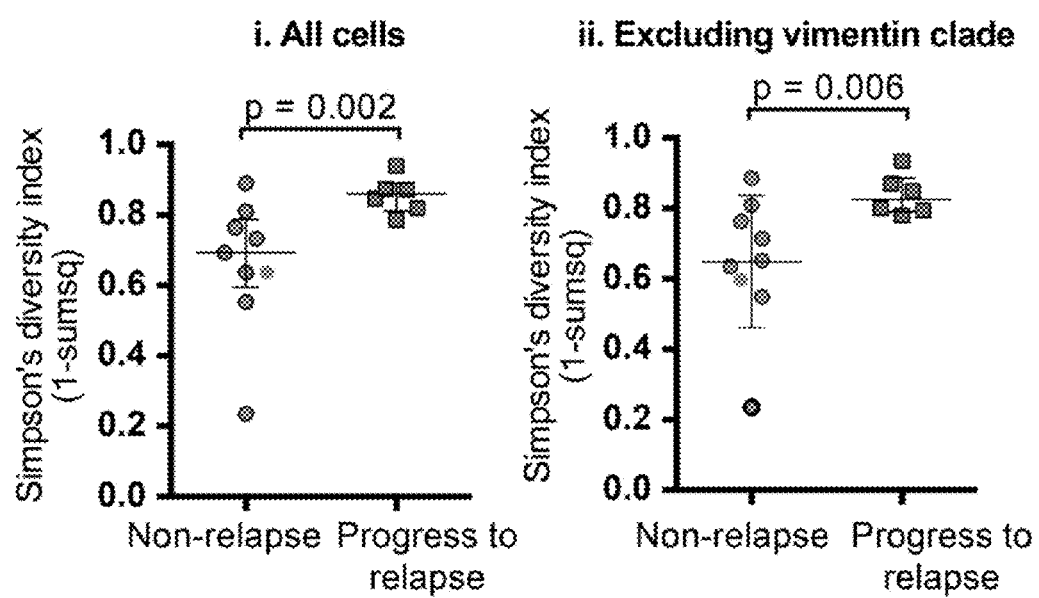

FIGS. 4A-4C show novel cell types and relationships in HG-SOC heterogeneity. FIG. 4A shows median protein expression levels (95% confidence intervals) for cells inside and outside the vimentin clade (light gray and dark gray plots respectively). Vimentin (p=)$1.62 \cdot 10^{-30}$), HE4 (p=0.0007) and cMyc (p=$2.3 \cdot 10^{-10}$) were expressed at significantly greater levels in the vimentin clade (asterisks). FIG. 4B shows manual-gating (representative samples shown) from the tumor cell parent population confirmed more cells co-expressing HE4 and cMyc in samples from patients that relapsed within one year (n=6) versus those that did not (n=9). FIG. 4C shows Simpson's index of diversity was significantly greater (p=0.0005) for samples that proceeded to relapse (n=5) versus those that did not (n=10). Medians and interquartile ranges are shown.

Figure 5A:
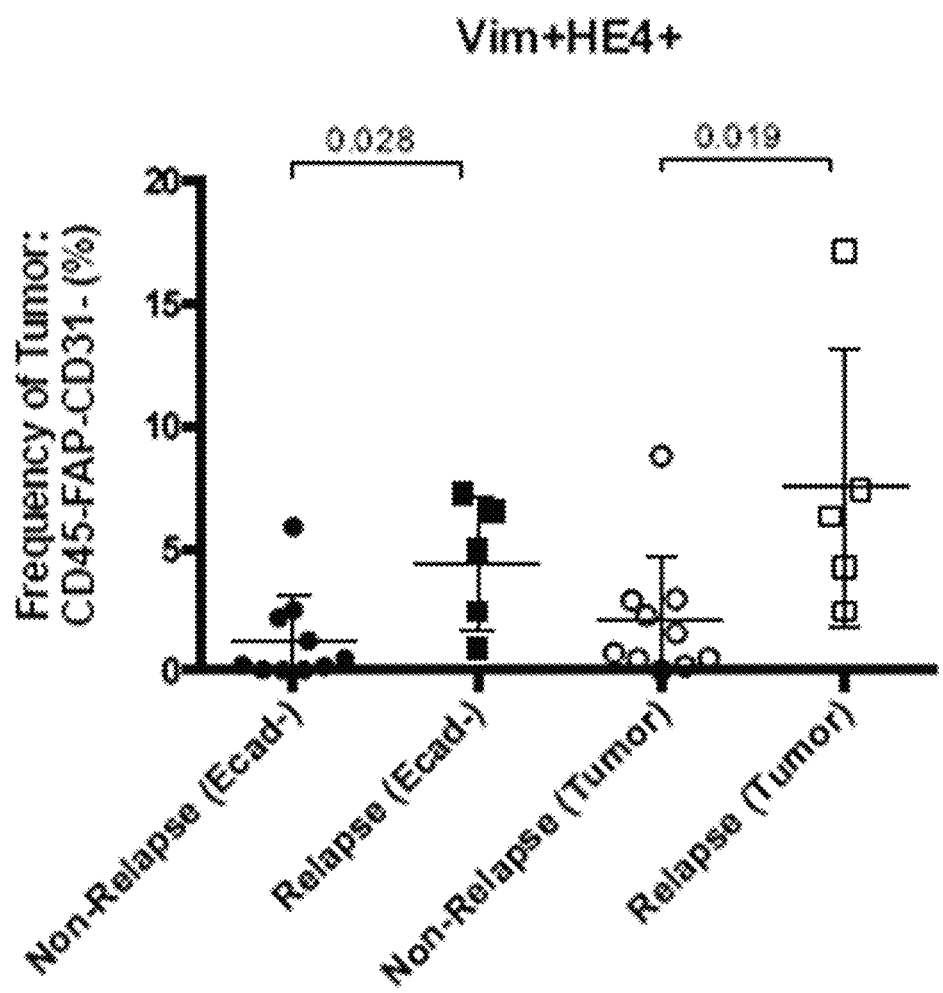
Figure 5B:
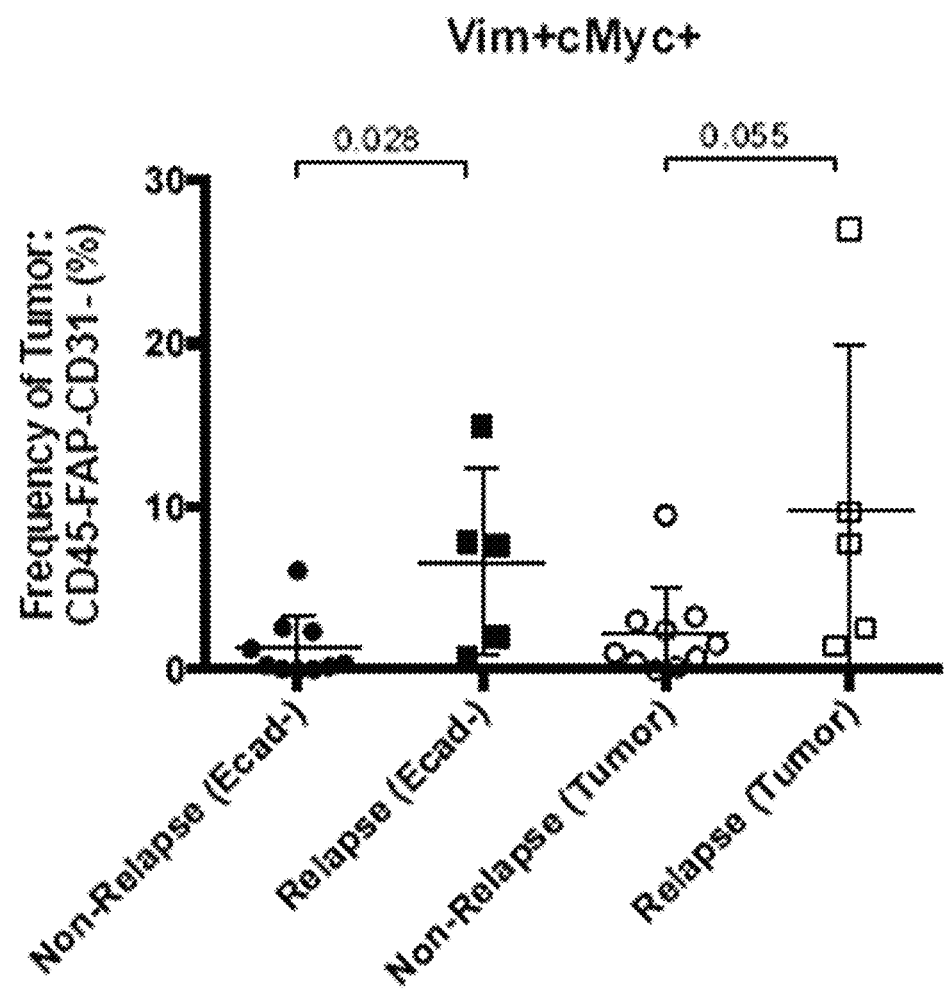
Figure 5C:
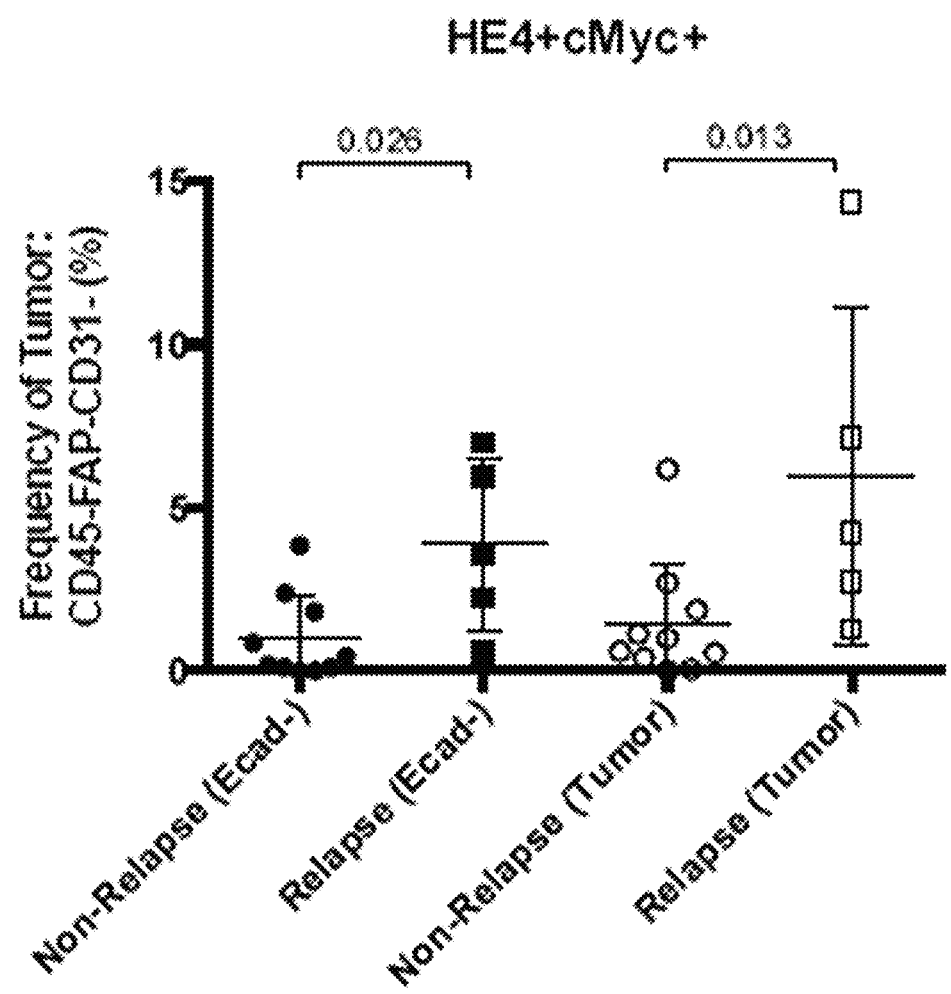

FIGS. 5A-5C show relapse samples enriched for cell subsets expressing vimentin, cMyc and HE4, including cells positive for vimentin and HE4 (FIG. 5A), cells positive for vimentin and cMyc (FIG. 5B), and cells positive for HE4 and cMyc (FIG. 5C).

Figure 6:
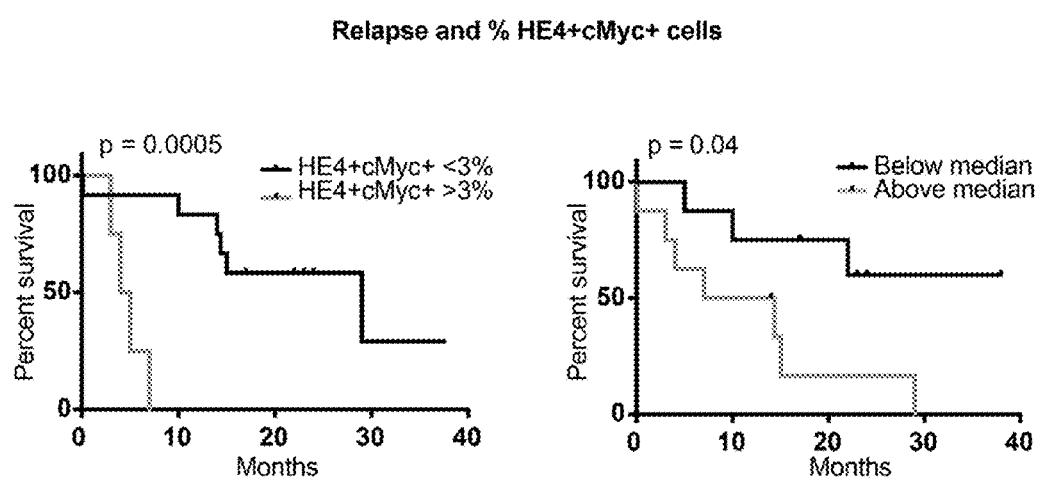

FIG. 6 shows Kaplan-Meier curves depicting differences in time-to-relapse for samples with greater than or less than two separately derived thresholds for cMyc/HE4 cells (log rank test, p=0.0005 (k-means) and p=0.04 (equal sized groups)).

Figure 7A:
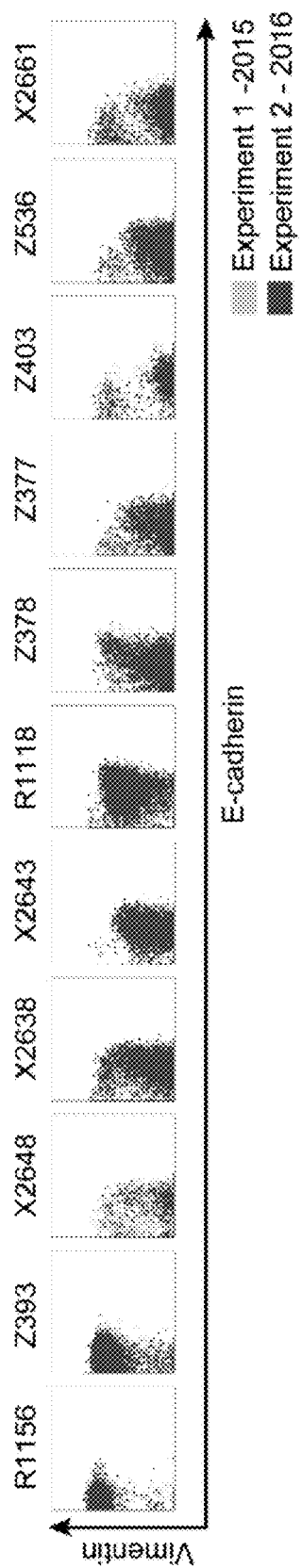
Figure 7B:
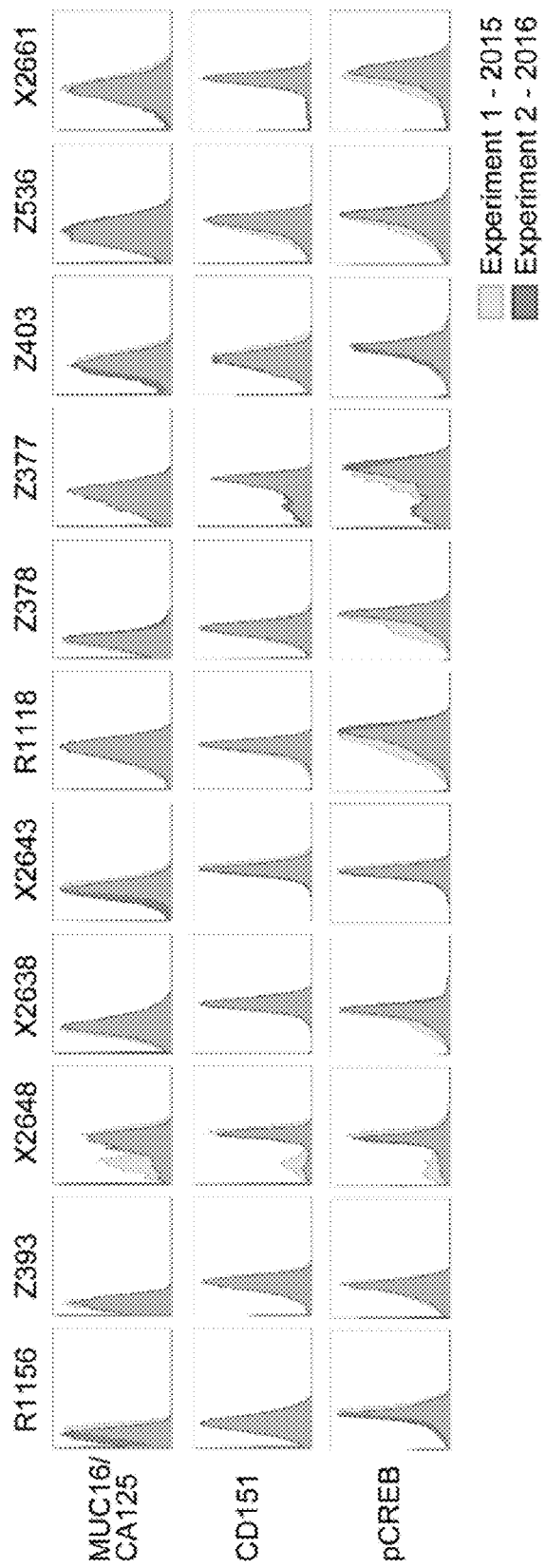

FIGS. 7A and 7B show replicates demonstrating that data was of the highest quality. Two CyTOF runs of the same samples were assayed about one year apart.

DETAILED DESCRIPTION

The practice of the present invention will employ, unless otherwise indicated, conventional methods of medicine, biology, biochemistry, recombinant DNA techniques, and immunology within the skill of the art. Such techniques are explained fully in the literature. See, e.g., *Ovarian Cancer with Expert Consult* (Early Diagnosis and Treatment of Cancer Series, R. E. Bristow and D. K. Armstrong eds., Saunders, 2009); *Advances in Diagnosis and Management of Ovarian Cancer* (S. Farghaly ed., Springer, 2014); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); and Sambrook et al., *Molecular Cloning: A Laboratory Manual* ($3^{rd}$ Edition, 2001).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes two or more cells, and the like.

The term "about," particularly in reference to a given quantity, is meant to encompass deviations of plus or minus five percent.

The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the protein, for example, glycosylation, acetylation, phosphorylation, hydroxylation, oxidation, and the like.

The phrase "differentially expressed" refers to differences in the quantity and/or the frequency of a marker present in a sample of ovarian tumor tissue or cells taken from patients having, for example, ovarian cancer that relapses as compared to those patients whose ovarian cancer does not relapse. For example, a marker can be a protein, which is present at an elevated level or at a decreased level in samples from patients with ovarian cancer that relapses compared to samples from patients whose ovarian cancer does not relapse. Alternatively, a marker can be a protein, which is detected at a higher frequency or at a lower frequency in samples from patients with ovarian cancer that relapses compared to samples from patients whose ovarian cancer does not relapse. A marker can be differentially present in terms of quantity, frequency or both.

A protein is differentially expressed between two samples if the amount of the protein in one sample is statistically significantly different from the amount of the protein in the other sample. For example, a protein is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a protein is differentially expressed in two sets of samples if the frequency of detecting the protein in samples of ovarian cancer patients who relapse, is statistically significantly higher or lower than in ovarian cancer patients who do not relapse. For example, a protein is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; $F_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

"Immunoassay" is an assay that uses an antibody to specifically bind an antigen (e.g., a marker). The immunoassay is characterized by the use of specific binding properties of a particular antibody to isolate, target, and/or quantify the antigen. An immunoassay for a protein marker may utilize one antibody or several antibodies. Immunoassay protocols may be based, for example, upon competition, direct reaction, or sandwich type assays using, for example, a labeled antibody. The labels may be, for example, fluorescent, chemiluminescent, or radioactive.

The phrase "specifically (or selectively) binds" to an antibody or "specifically (or selectively) immunoreactive with," when referring to a protein or peptide, refers to a binding reaction that is determinative of the presence of the protein marker in a heterogeneous population of proteins and other biologics. Thus, under designated immunoassay conditions, the specified antibodies bind to a particular protein marker at least two times the background and do not substantially bind in a significant amount to other proteins present in the sample. Specific binding to an antibody under such conditions may require an antibody that is selected for its specificity for a particular protein marker. For example, polyclonal antibodies raised to a protein marker from specific species such as rat, mouse, or human can be selected to obtain only those polyclonal antibodies that are specifically immunoreactive with the protein marker and not with other proteins, except for polymorphic variants and alleles of the protein marker. This selection may be achieved by subtracting out antibodies that cross-react with biomarker molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Capture reagent" refers to a molecule or group of molecules that specifically bind to a specific target molecule or group of target molecules. For example, a capture reagent can comprise two or more antibodies each antibody having specificity for a separate target molecule. Capture reagents can be any combination of organic or inorganic chemicals, or biomolecules, and all fragments, analogs, homologs, conjugates, and derivatives thereof that can specifically bind a target molecule.

The capture reagent can comprise a single molecule that can form a complex with multiple targets, for example, a multimeric fusion protein with multiple binding sites for different targets. The capture reagent can comprise multiple molecules each having specificity for a different target, thereby resulting in multiple capture reagent-target complexes. In certain embodiments, the capture reagent is comprised of proteins, such as antibodies.

The capture reagent can be directly labeled with a detectable moiety. For example, an anti-marker antibody can be directly conjugated to a detectable moiety and used in the inventive methods, devices, and kits. In the alternative, detection of the capture reagent-marker complex can be by a secondary reagent that specifically binds to the marker or the capture reagent-marker complex. The secondary reagent can be any biomolecule, and is preferably an antibody. The secondary reagent is labeled with a detectable moiety. In some embodiments, the capture reagent or secondary reagent is coupled to biotin, and contacted with avidin or streptavidin having a detectable moiety tag.

"Detectable moieties" or "detectable labels" contemplated for use in the invention include, but are not limited to, radioisotopes such as such as $^3$H, $^{14}$C, $^{32}$P and $^{125}$I; metal isotopes such as rare earth elements, including cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y); fluorescent dyes such as SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, rhodamine, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), FITC, dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, *Renilla* luciferase, and aequorin. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Diagnosis" as used herein generally includes determination as to whether a subject is likely affected by a given disease, disorder or dysfunction. The skilled artisan often makes a diagnosis on the basis of one or more diagnostic indicators, i.e., a marker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; primates, and transgenic animals.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of cellular markers associated with a poor prognosis for ovarian cancer patients. In particular, the inventors have shown that increased frequency of a subset of cells within ovarian tumors expressing the cellular markers vimentin, Myc and HE4 is associated with relapse within one year (see Examples 1 and 2). In order to further an understanding of the invention, a more detailed discussion is provided below regarding methods of using these cellular markers in prognosis and monitoring treatment of ovarian cancer.

A. Cellular Markers Prognostic of Ovarian Cancer Recurrence

In one aspect, the invention includes a prognostic method for predicting whether an ovarian cancer patient will relapse. The method typically comprises: a) obtaining a sample of ovarian tumor tissue or cells from the patient; b) measuring frequency of cells expressing one or more markers selected from the group consisting of vimentin, cMyc and HE4 in the sample; and c) comparing the frequency of cells expressing said markers in the sample to respective reference value ranges for said markers for ovarian cancer patients who do not relapse, wherein increased frequency of the one or more markers selected from the group consisting of vimentin, cMyc and HE4 compared to the reference value ranges for the markers for ovarian cancer patients who do not relapse indicates the patient will relapse within 1 year. Thus, increased frequency of cells positive for vimentin and HE4, cells positive for vimentin and cMyc, cells positive for HE4 and cMyc, or cells positive for vimentin, HE4, and cMyc compared to the reference value ranges for ovarian cancer patients who do not relapse indicates increased likelihood that the ovarian cancer patient will relapse. In addition, increased frequency of cells positive for vimentin and having higher levels of expression of cMyc and HE4 compared to reference value ranges for the markers for ovarian cancer patients who do not relapse further indicates increased likelihood that the ovarian cancer patient will relapse. The ovarian cancer patient is predicted to relapse if the frequency of cells positive for one or more of the markers selected from the group consisting of vimentin, cMyc and HE4 is greater than 1%.

When analyzing the frequencies of cells carrying the cellular markers vimentin, cMyc and HE4 in a sample of ovarian tissue or cells, the reference value ranges used for comparison can represent the frequencies of ovarian tumor cells carrying one or more of the cellular markers in one or more samples from one or more ovarian cancer patients who have ovarian cancer that did not relapse. Alternatively, the reference value ranges can represent the frequencies of ovarian tumor cells carrying one or more of the cellular markers in one or more samples from one or more patients who have ovarian cancer that relapsed.

In another embodiment, the method further comprises detecting whether the cells having increased frequency of one or more of the vimentin, cMyc, and HE4 markers are E-cadherin negative cells. Absence of E-cadherin in the cells carrying one or more of the vimentin, cMyc and HE4 markers indicates an increased likelihood of ovarian cancer relapse compared to if the cells are E-cadherin positive.

The sample obtained from the patient to be diagnosed is typically a biopsy of abnormal tissue suspected of containing cancerous cells, but may also include tissue from a surgical resection of a tumor. In certain embodiments, the sample may comprise a tissue sample including a portion, piece, part, segment, or fraction of tissue, which is obtained or removed from intact ovarian tissue of a patient. The sample can be obtained from the patient by conventional techniques. For example, a tissue biopsy may be obtained by methods including, but not limited to, an aspiration biopsy, a brush biopsy, a surface biopsy, a needle biopsy, a punch biopsy, an excision biopsy, an open biopsy, an incision biopsy or an endoscopic biopsy.

A "control" sample, as used herein, refers to a sample of ovarian tissue or cells that are not diseased. That is, a control sample is obtained from a normal subject (e.g. an individual known to not have cancer or any condition or symptom associated with abnormal cell maturation or proliferation).

The methods described herein may be used to determine if an ovarian cancer patient is at high risk of relapse within one year and in need of immediate medical intervention, or at lower risk and can be further monitored before treatment. Both patients and clinicians can benefit from better estimates of relapse risk, which allows timely discussions of patients' preferences and their choices regarding life-saving measures.

Treatment of a patient, identified as having a high risk of ovarian cancer recurrence (i.e., relapse), may comprise surgery, radiation therapy, chemotherapy, targeted therapy, anti-angiogenic therapy, or immunotherapy, or any combination thereof.

For example, treatment by surgery may comprise a unilateral oophorectomy, a bilateral oophorectomy, or a salpingo oophorectomy.

Treatment by chemotherapy may comprise administering, for example, a platinum or a nonplatinum chemotherapeutic agent, or a combination thereof. Exemplary chemotherapeutic agents for treatment of ovarian cancer include paclitaxel, cisplatin, topotecan, doxorubicin, epirubicin, gemcitabine, docetaxel, carboplatin, and taxol. In one embodiment, chemotherapy comprises administering a platinum chemotherapeutic agent and taxol.

Treatment by immunotherapy may comprise administering, for example, an immune-modulatory agent, such as, but not limited to, an anti-PD1 agent such as pembrolizumab; an anti-PDL1 agent such as durvalumab; a Toll-like receptor 8 agonist such as motolimod; an anti-CTLA4 agent, such as tremelimumab, and an IDO1 inhibitor such as nivolumab, or an ovarian cancer vaccine or adoptive T cell transfer.

Treatment by targeted therapy may comprise administering, for example, one or more small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax and gossypol; PARP inhibitors, such as Iniparib and Olaparib; PI3 kinase inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar); bromodomain and extra-terminal (BET) family inhibitors, such as JQ1, I-BET 151, I-BET 762, OTX-015, TEN-010, CPI-203, CPI-0610, RVX-208, and LY294002; and monoclonal antibodies, such as farletuzumab, mirvetuximab soravtansine, mirvetuximab soravtansine, mirvetuximab soravtansine, IMMU-132, DNIB0600A, DNIB0600A, demcizumab (OMP-21M18), and monalizumab. In certain embodiments, targeted therapy comprises administering a poly-(ADP)-ribose polymerase (PARP) inhibitor, a PI3 kinase inhibitor, or a targeted bromodomain and extra-terminal (BET) family inhibitor, or a combination thereof.

Treatment by anti-angiogenic therapy may comprise administering a vascular endothelial growth factor (VEGF) inhibitor such as bevacizumab.

The methods of the invention are also useful for monitoring the efficacy of a therapy for treating ovarian cancer in a patient. The efficacy of a therapy for treating ovarian cancer can be monitored, for example, by measuring the frequency of cells expressing one or more markers selected from the group consisting of vimentin, cMyc and HE4 in a first sample of ovarian tumor tissue or cells derived from the patient before the patient undergoes the therapy and a second sample of ovarian tumor tissue or cells derived from the patient after the patient undergoes the therapy, wherein increased frequency of cells expressing the one or more markers selected from the group consisting of vimentin, cMyc and HE4 in the second sample compared to the frequency of cells expressing the markers in the first sample indicates that the patient is worsening, and decreased frequency of cells expressing the one or more markers selected from the group consisting of vimentin, cMyc and HE4 in the second sample compared to the frequency of cells expressing the markers in the first sample indicates that the patient is improving. For example, increased frequency of cells positive for vimentin and HE4, cells positive for vimentin and cMyc, cells positive for HE4 and cMyc, or cells positive for vimentin, HE4, and cMyc in the second sample compared to their frequency in the first sample indicates that the patient is worsening. In certain embodiments, the method further comprises detecting whether the cells having increased frequency of the one or more markers selected from the group consisting of vimentin, cMyc and HE4 are E-cadherin negative cells, wherein absence of the E-cadherin in the cells indicates increased likelihood that the ovarian cancer patient will relapse compared to if the cells are E-cadherin positive.

B. Detecting Cellular Markers

It is understood that the cellular markers in a sample can be detected by any suitable method known in the art, including, but not limited to, mass cytometry, flow cytometry, immunohistochemistry, immunofluorescence, multiplexed ion beam imaging (MIBI), or other multi-parametric single cell analysis technology.

In particular, flow cytometry can be used to distinguish subpopulations of cells expressing different cellular markers and to determine their frequency in a population of cells. Typically, whole cells are incubated with antibodies that specifically bind to the cellular markers. The antibodies can be labeled, for example, with a fluorophore, isotope, or quantum dot to facilitate detection of the cellular markers. The cells are then suspended in a stream of fluid and passed through an electronic detection apparatus. In addition, fluorescence-activated cell sorting (FACS) can be used to sort a heterogeneous mixture of cells into separate containers. (See, e.g., Shapiro *Practical Flow Cytometry*, Wiley-Liss, 4$^{th}$ edition, 2003; Loken *Immunofluorescence Techniques in Flow Cytometry and Sorting*, Wiley, 2$^{nd}$ edition, 1990; *Flow Cytometry: Principles and Applications*, (ed. Macey), Humana Press 1$^{st}$ edition, 2007; herein incorporated by reference in their entireties.)

Cytometry by time-of-flight (CyTOF), also known as mass cytometry, is another method that can be used for detection of cellular markers in whole cells. CyTOF uses transition element isotopes as labels for antibodies, which are detected by a time-of-flight mass spectrometer. Unlike conventional flow cytometry, CyTOF is destructive to cells, but has the advantage that it can be used to analyze more cell markers simultaneously. See, e.g., Bendall et al. (2012) Trends in Immunology 33:323-332; Newell et al. (2012) Immunity 36(1):142-52; Ornatsky et al. (2010) J. Immunol. Methods 361 (1-2):1-20; Bandura et al. (2009) Analytical Chemistry 81:6813-6822; Chen et al. (2012) Cell Mol. Immunol. 9(4):322-323; and Cheung et al. (2011) Nat. Rev. Rheumatol. 7(9):502-3; herein incorporated by reference in their entireties.

In addition, multiplexed ion beam imaging (MIBI) can be used to distinguish subpopulations of cells carrying different cellular markers. MIBI uses secondary ion mass spectrometry to image antibodies that are tagged with isotopically pure elemental metal reporters. Not only can MIBI measure protein levels on individual cells, but also, the technique is capable of providing information about cell morphology and localization. Like CYTOF, MIBI is capable of analyzing a large number of cell markers (e.g., up to 100) simultaneously over a five-log dynamic range. See, e.g., Angelo et al.

(2014) Nat. Med. 20(4):436-442; Bodenmiller et al. (2016) Cell Syst. 2(4):225-238; and Levenson et al. (2015) Lab Invest. 95(4):397-405; herein incorporated by reference in their entireties.

Immunohistochemistry can be used to detect marker antigens in cells of a tissue section. For example, immunohistochemical staining with labeled antibodies can be used to detect the vimentin, cMyc or HE4 on ovarian cells. Antibodies conjugated to enzymes, which catalyze color-producing reactions with chromogenic, fluorogenic, or chemiluminescent substrates (e.g., alkaline phosphatase or peroxidase), are commonly used. Alternatively, immunohistochemical staining can be performed with antibodies conjugated to fluorophores (e.g., fluorescein or rhodamine) to visualize markers. See, e.g., Dabbs *Diagnostic Immunohistochemistry: Theranostic and Genomic Applications*, Saunders, $3^{rd}$ edition, 2010; Chu *Modern Immunohistochemistry* (Cambridge Illustrated Surgical Pathology) Cambridge University Press, 2009; Buchwalow et al. Immunohistochemistry: Basics and Methods, Springer, 1st Edition, 2010; and Ramos-Vara (2011) Methods Mol. Biol. 691:83-96; herein incorporated by reference in their entireties.

Antibodies that specifically bind to a cellular marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). A protein marker antigen can be used to immunize a mammal, such as a mouse, rat, rabbit, guinea pig, monkey, or human, to produce polyclonal antibodies. If desired, a marker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a protein marker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 31 42, 1985; Cote et al., Proc. Natl. Acad. Sci. 80, 2026-30, 1983; Cole et al., Mol. Cell Biol. 62, 109-20, 1984).

In addition, techniques developed for the production of "chimeric antibodies," the splicing of mouse antibody genes to human antibody genes to obtain a molecule with appropriate antigen specificity and biological activity can be used (Morrison et al., Proc. Natl. Acad. Sci. 81, 6851-55, 1984; Neuberger et al., Nature 312, 604-08, 1984; Takeda et al., Nature 314, 452-54, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332. Human monoclonal antibodies can be prepared in vitro as described in Simmons et al., PLoS Medicine 4(5), 928-36, 2007.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, Proc. Natl. Acad. Sci. 88, 11120-23, 1991).

Single-chain antibodies also can be constructed using a DNA amplification method, such as PCR, using hybridoma cDNA as a template (Thirion et al., Eur. J. Cancer Prev. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J Cancer 61, 497-501, 1995; Nicholls et al., J. Immunol. Meth. 165, 81-91, 1993).

Antibodies which specifically bind to a marker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Antibodies may be used in diagnostic assays to detect the presence or for quantification of the markers in a biological sample. Such a diagnostic assay may comprise at least two steps; (i) contacting a sample comprising ovarian tissue or cells with the antibody and (ii) quantifying the antibody bound to the cellular marker antigen. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, or $^{125}$I, a fluorescent or chemiluminescent compound, such as fluorescein isothiocyanate, rhodamine, or luciferin, a fluorescent protein, such as a green fluorescent protein, red fluorescent protein, or yellow fluorescent protein, an enzyme, such as alkaline phosphatase, beta-galactosidase, or horseradish peroxidase, or a metal isotope, such as a rare earth element (e.g., cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y)). Any method known in the art for conjugating the antibody to the detectable moiety may be employed, including those methods described by Hunter et al., Nature, 144:945 (1962); David et al., Biochem., 13:1014 (1974); Pain et al., J. Immunol. Methods, 40:219 (1981); and Nygren, J. Histochem. and Cytochem. 30:407 (1982).

The number of cells in a biological sample can be determined by any suitable method known in the art, including visual counting of cells observed microscopically or automated methods of cell counting. For example, cells can be counted by using a flow cytometer, Coulter counter, CASY counter, hemocytometer, or microscopic imaging. Cells can be distinguished by their shape, intracellular structures, staining characteristics, as well as the presence of cellular markers.

For example, various visual counting methods can be used. A hemocytometer can be used to count cells viewed under a microscope. The hemocytometer contains a grid to allow manual counting of the number of cells in a certain area and a determination of the concentration of cells in a sample. Alternatively, cells can be plated on a petri dish containing a growth medium. The cells are plated at a dilution such that each cell gives rise to a single colony. The colonies can then be visually counted to determine the number and frequency of particular cells types present in a sample.

Automated cell counting can be performed with a flow cytometer, Coulter counter, CASY counter, or by automated microscopic imaging analysis. Coulter and CASY counters can be used to measure the volumes and numbers of cells. Flow cytometry can be used for automated cell counting and sorting and for detecting surface and intracellular markers. Additionally, microscopic analysis of cells can be automated. For example, microscopy images can be analyzed using statistical classification algorithms that automate cell detection and counting. See, e.g., Shapiro (2004) Cytometry A 58(1):13-20; Glory et al. (2007) Cell Mol. Biol. 53(2): 44-50; Han et al. (2012) Machine Vision and Applications 23 (1): 15-24; herein incorporated by reference.

C. Kits

In yet another aspect, the invention provides kits for predicting whether an ovarian cancer patient will relapse. For example, the kits can be used to detect or measure any one or more of the cellular markers vimentin, cMyc, and HE4 in order to determine the frequency of cells expressing one or more of these cellular markers in a sample of ovarian tumor tissue or cells from a patient. The kit may include one or more agents for measuring the cellular markers, a container for holding a biological sample comprising ovarian tumor tissue or cells isolated from a human subject; and printed instructions for reacting agents with the sample or a portion of the sample to detect one or more of the cellular markers. The agents may be packaged in separate containers. The kit may further comprise one or more control reference samples and reagents for performing mass cytometry, flow cytometry, immunohistochemistry, immunofluorescence, multiplexed ion beam imaging (MIBI), or other multi-parametric single cell analysis technology.

In certain embodiments, the kit comprises a set of antibodies comprising an antibody that specifically binds to vimentin, an antibody that specifically binds to cMyc, and an antibody that specifically binds to HE4. Antibodies in the kit may be conjugated to a detectable label to facilitate detection of the marker on cells such as a metal isotope or fluorescent label. In one embodiment, each antibody is conjugated to a metal isotope suitable for performing mass cytometry or multiplexed ion beam imaging (MIBI), such as a rare earth element.

In another embodiment, the kit further comprises an antibody that specifically binds to E-cadherin. Such an antibody may also be conjugated to a detectable label to facilitate detection of the marker on cells, such as a metal isotope suitable for performing mass cytometry or multiplexed ion beam imaging (MIBI) or a fluorescent label.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for measuring the frequency of cells carrying one or more of the vimentin, cMyc, and HE4 cellular markers and predicting the likelihood that an ovarian cancer patient will relapse.

In another embodiment, the kit further comprises a computer model or algorithm for analyzing the frequency of cells expressing one or more markers selected from the group consisting of the vimentin, cMyc, or HE4 in a sample of ovarian tumor tissue or cells from a patient in order to determine the likelihood that an ovarian cancer patient will relapse.

The kits of the invention have a number of applications. For example, the kits can be used in prognosis to determine if ovarian cancer recurrence is likely to occur within one year. In addition, the kits can be used to monitor the effectiveness of treatment of a patient for ovarian cancer.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

New Tumor Types Revealed in Ovarian Cancer by High-Dimensional Mass Cytometric Profiling Introduction High-grade serous ovarian cancer (HG-SOC) has been treated clinically as a single disease with most patients receiving the same standard-of-care therapies (Liu & Matulonis (2014) Clin Cancer Res 20:5150-5156), even though genetic, molecular and protein expression studies indicate that HG-SOC tumors display a high degree of inter- and intra-tumor heterogeneity (Integrated genomic analyses of ovarian carcinoma. Cancer Genome Atlas Research Network (2011) Nature 474:609-615; Bowtell et al. (2015) Nat. Rev. Cancer 15:668-679; Patch et al. (2015) Nature 521: 489-494). This is underscored by the fact there is a paucity of predictive and prognostic mechanistic markers that truly reflect HG-SOC pathophysiology. To gain deeper insight into HG-SOC heterogeneity we studied primary ovarian tumors using mass cytometry, a high-dimensional single cell technology that facilitates the identification of rare cell types that would be masked in analyses of tumors processed in bulk (Bendall et al. (2011) Science 332:687-696; Bjornson et al. (2013) Curr. Opin. Immunol. 25:484-494). With a panel of antibodies, each conjugated to a distinct stable metal isotope, mass cytometry currently enables the simultaneous acquisition of up to 50 measurements per single cell. Here, we present the most comprehensive single cell phenotypic characterization of primary HG-SOC simultaneously measuring expression of surface markers, intracellular signaling and cell cycle states. Our data-driven analyses reveal the substructure of the disease. The validity of the experimental approach was evidenced by confirmation of well-established facets of epithelial tumor biology (Davidson et al. (2012) Front Oncol. 2:33; Nieto (2013) Science 342:1234850; Ye & Weinberg (2015) Trends Cell Biol. 25:675-686). However also revealed, based on protein co-expression combinations, were cell types not previously recognized. We observed three distinct E-cadherin-expressing cell subsets occurring repeatedly across multiple HG-SOC samples and cell subsets co-expressing E-cadherin and vimentin, including one subset that co-expressed high levels of all stem cell markers interrogated. Poorer prognosis tumors had an increased frequency of cells co-expressing vimentin with HE4 and cMyc as well as greater overall phenotypic heterogeneity quantified by Simpson's Diversity Index. The methodology we describe and the systems level view of cell types revealed by mass cytometry has the potential to allow a re-evaluation of the composition of HG-SOCs and other cancers and, in doing so, allow the most beneficial therapeutic regimens to be selected.

Results

Figure 1:
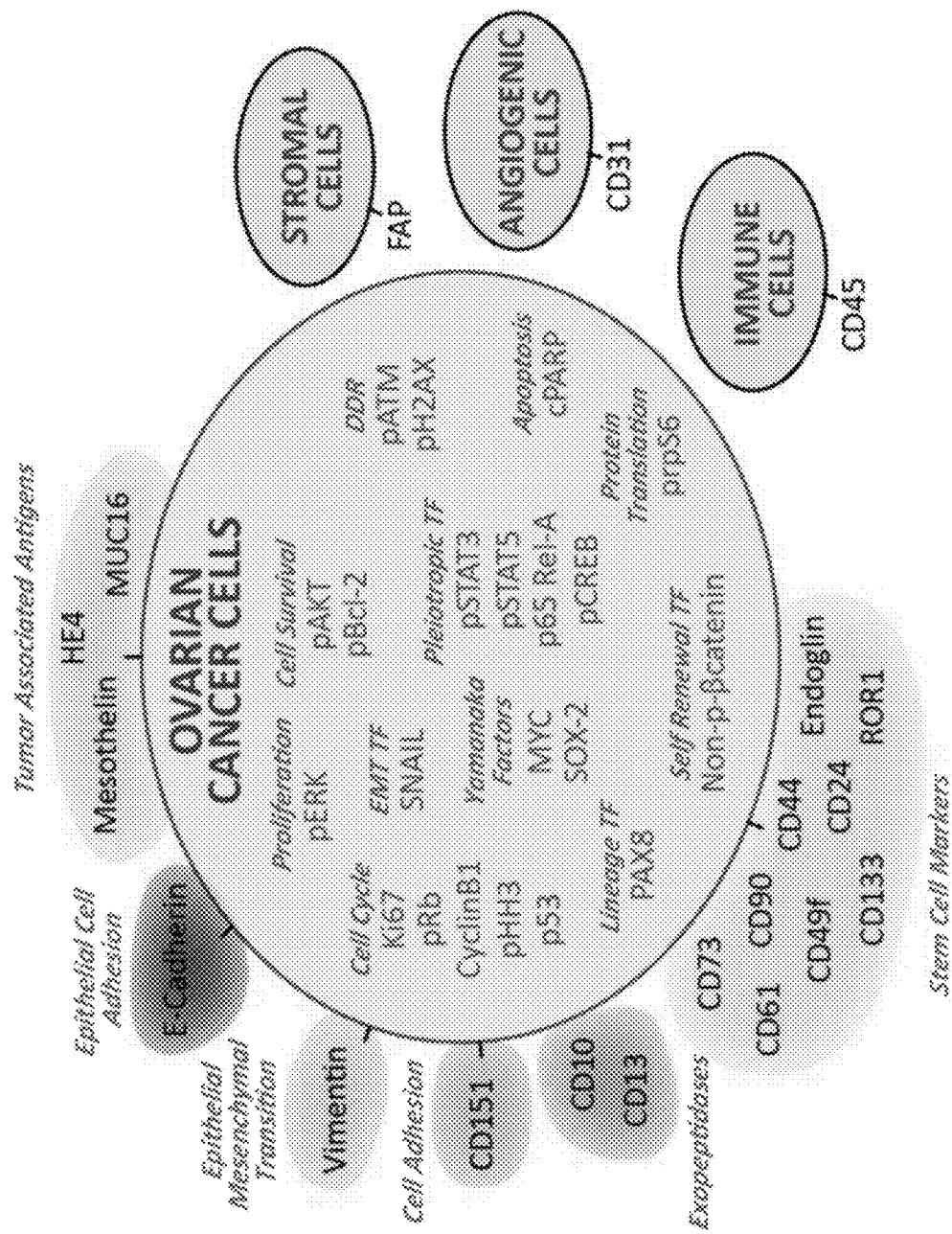
FIG. 1 shows an antibody panel for mass cytometry. Antibodies (38) selected to interrogate cellular proteins in ovarian tumor single cell suspensions are shown. Shading indicates different categories of proteins. Additionally, antibodies to CD45, FAP and CD31 were included in the panel to identify and subsequently exclude immune, angiogenic and stromal cells from analysis as no prior sorting of the sample took place before mass cytometry.
Figure 2A:
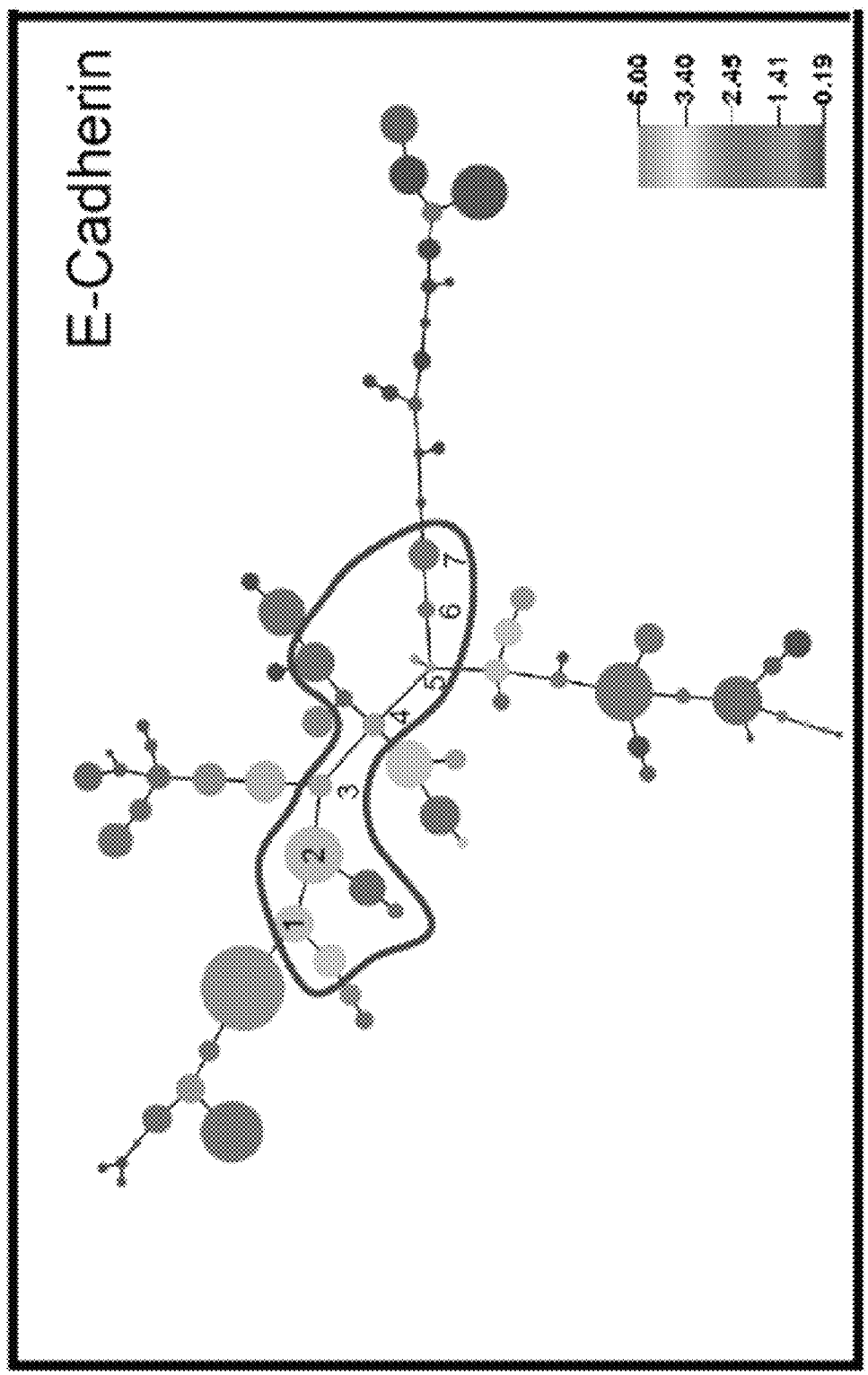
FIGS. 2A and 2B show median protein expression levels of cell clusters computationally arranged on minimum spanning trees (MSTs). A composite MST of the 22 tumors shows median expression of E-cadherin (E) and vimentin (V) (right-hand panel). Thirteen cell clusters co-expressing E and V (EV clusters) are encircled. The size of each bubble represents the number of cells in the cluster and is $$\sqrt[3]{\text{absolute number of cells from all samples}}.$$
Figure 2B:
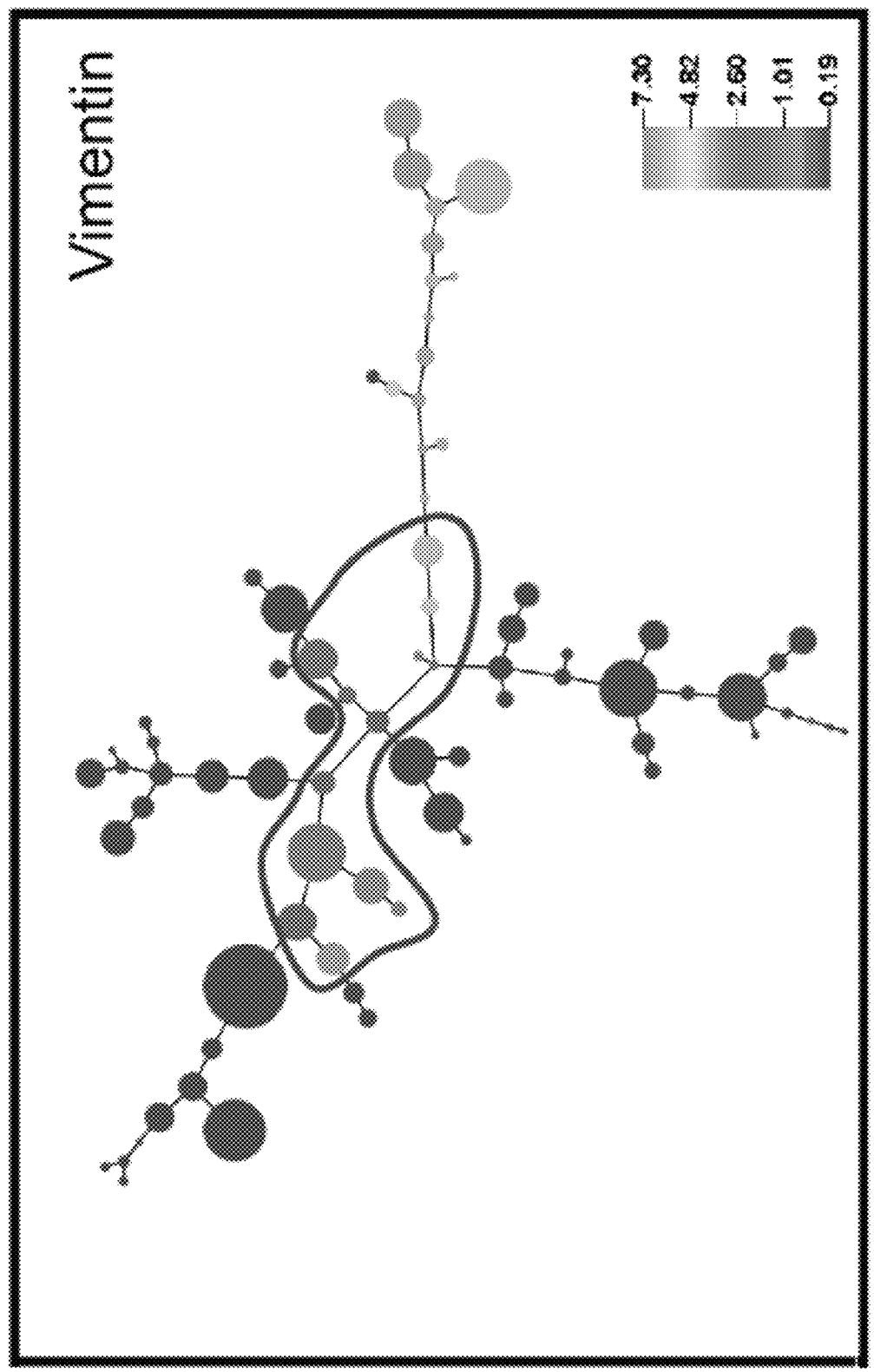

Primary chemotherapy-naive ovarian tumor samples, with a median follow-up of 21.5 months and characterized by genomic sequence analysis for BRCA1, BRCA2 and TP53, were subjected to stringent protocols optimized to generate viable single cell suspensions after surgical resection (Methods). Tumor sections were analyzed by immunohistochemistry (IHC) to allow subsequent comparison with single cell data (Methods, Table 4). Single cell suspensions of tumor cells were analyzed by mass cytometry which is based on the detection of stable-metal isotopes (that are rare or absent in biological samples) conjugated to antibodies bound to cells (Bendall et al. (2011) Science 332:687-696; Bjornson et al. (2013) Curr Opin Immunol 25:484-494). A panel of 41 antibodies, designed to interrogate key features of HG-SOC tumor-cell biology (FIG. 1, Methods) were utilized (Bowtell et al., supra; Davidson et al., supra; Ye & Weinberg, supra; Davidowitz et al. (2014) J. Clin. Invest. 124:2611-2625; Stewart et al. (2011) Proc. Natl. Acad. Sci. U.S.A. 108:6468-6473; Zhang et al. (2014) Proc. Natl. Acad. Sci. U.S.A. 111:17266-17271; Baldwin et al. (2014) Oncotarget 5:12203-12217; Lu et al. (2012) Biochem. Biophys. Res. Commun. 419:274-280). This analysis, focused on tumor cells, excluded immune, stromal and angiogenic cells by manual gating (Methods). Initially, single-cell readouts for each of 22 primary ovarian tumors were computationally merged without input of biological or clinical features. Subsequently, tumor cells were clustered with a new fast non-parametric density-based algorithm called X-shift (Samusik et al. (2016) Nat. Methods 13(6):493-496) according to their co-expression patterns for the markers E-cadherin, CD73, CD61, CD90, CD151, CD49f, CD133, ROR1, CD10, CD13, endoglin, CD24, CD44, MUC16 (CA125), mesothelin, vimentin, and HE4 (FIG. 1). The resultant X-shift clusters, were computationally arranged on a minimum spanning tree (MST) (Samusik, N., Good, Z, Spitzer, M, Davis, K L, Nolan, G P. Automated Mapping of Phenotype Space with Single-cell Data. Submitted (2016)) such that those with the most similar co-expression patterns of the protein markers listed above were placed adjacent to one another (FIGS. 2A and 2B; Samusik et al., supra). Such MSTs enabled the visualization of a detailed substructure of the different cell subtypes occurring within the tumor samples (FIGS. 2A and 2B). HG-SOC is an epithelial cancer with cells in the primary tumor tightly bound by intercellular junctions, of which E-cadherin is a requisite component (Davidson et al., supra). For cells to metastasize they need to acquire migratory properties and undergo epithelial to mesenchymal transition (EMT) (Davidson et al., supra; Ye & Weinberg, supra). This requires repression of E-cadherin expression and other cell-cell junction components with concomitant expression of vimentin intermediate filaments, the latter being a hallmark of the mesenchymal state (Davidson et al., supra; Ye & Weinberg, supra).

The composite MST of all 22 HG-SOC tumor samples showed that the tumors predominantly expressed E-cadherin which was essentially mutually exclusive with vimentin expression (FIGS. 2A and 2B). Notably, 13 cell clusters co-expressed E-cadherin and vimentin (EV clusters), some of which formed a bridge in the map in which E-cadherin levels declined concomitantly with increased vimentin expression (FIGS. 2A and 2B, encircled and numbered). Furthermore, SNAIL a master coordinator of EMT, was also frequently expressed in these "bridge" clusters (Davidson et al., supra; Ye et al. (2015) Nature 525:256-260).

Recent data support the link between transit through EMT and the acquisition of stem cell-like properties (Ye & Weinberg (2015) Trends Cell Biol. 25:675-686; Islam et al. (2015) Exp. Cell Res. 335:135-147; Scheel & Weinberg (2012) Semin. Cancer Biol. 22:396-403). Consistent with this, the cancer stem cell markers included in this study (CD24, CD13, CD10, CD73, CD61, CD49f, CD90, CD44, CD133, endoglin, ROR1), as well as signaling proteins involved in conferring stemness (Sox-2, pSTAT3, pSTAT5, NFκB, pCREB and β-catenin; Ajani et al. (2015) Semin Oncol 42 Suppl 1:S3-17, Boumandi et al. (2014) Nature 511:246-250, Pattabiraman & Weinberg (2014) Nat. Rev. Drug Discov. 13:497-512), were detected in the EV clusters. With one exception, EV1, varying levels and differing combinations of these markers were seen. EV1 was notable for expressing, frequently at increased levels, all the "stemness" markers interrogated (as well as other proteins) suggesting these cells may have reached or are transitioning through an important checkpoint for outgrowth in the tumor compartment or for gaining metastatic traits. In other branches of the MST, the many proteins co-expressed (in differing combinations and intensities) included stemness proteins, cell cycle proteins, DNA damage sensors and CD151, a key regulator of adhesion implicated in metastatic progression of ovarian cancer (Bowtell et al., supra; Patch et al., supra; Baldwin et al., supra; Ajani et al., supra). This observed phenotypic heterogeneity within the epithelial compartment supports the model that non-cell autonomous interactions are a prerequisite for tumor growth and development (Marusyk et al. (2014) Nature 514:54-58).

TP53, known to be mutated in up to 95% HG-SOCs (Integrated genomic analyses of ovarian carcinoma, Nature 474:609-615; Bowtell et al., supra), was expressed in epithelial and EV tumor cells with mutational status associated with protein expression. However, three HG-SOC tumors with wild type sequence expressed TP53 protein by an unknown mechanism. PAX8, MUC16 (CA125) and mesothelin, also recognized to be associated with HG-SOC were confined to epithelial and EV tumor cells and were not detected in vimentin-expressing cell clusters (Bowtell et al., supra). HE4, an ovarian tumor-associated protein, with a role in cellular migration, was also expressed in the E-cadherin and EV clusters, but was noteworthy for its co-expression with cMyc in the vimentin-expressing branch of the MST (Lu et al., supra; Gabay et al. (2014) Cold Spring Harb Perspect Med 4; Lawson et al. (2015) Nature 526:131-135). Although, cMyc and HE4 amplification is well-documented in HG-SOC, their co-expression with vimentin is a new finding and suggests that they may have a prominent role in HG-SOC metastasis (Integrated genomic analyses of ovarian carcinoma. Cancer Genome Atlas Research Network (2011) Nature 474:609-615; Bowtell et al., supra; Lu et al., supra; Gabay et al., supra; Lawson et al., supra). In this regard, HE4 when measured in blood together with MUC16 has been reported to provide a more accurate predictor of malignancy than MUC16 alone (Lu et al., supra).

Examination of the MSTs on a per-sample basis gives insight into the heterogeneity of the tumors of individual patients. Reflecting the observations for the composite MSTs, the majority of individual samples were enriched for E-cadherin-rather than vimentin-expressing cell clusters. Examination of the relative cell frequency distribution across all clusters on a per-sample basis revealed that there were three repeatedly occurring clusters (termed CC 1, 2 and 3) that were located within the E-cadherin-expressing portion of the tumor (FIGS. 3A, B). Furthermore, for sixteen samples at least 10% of all tumor cells occupied one of these CCs and this cell frequency distribution within a CC was often much higher such that in some cases most cells within a sample occupied a CC (FIG. 3A). For samples 13, 16 and 19 the cell frequency distribution within CC1, 2 or 3 was less than 10% with alternate clusters dominating these samples suggesting that these three tumors may have a different heterogeneity structure (FIG. 3A). Furthermore, the divergent MSTs observed for samples 20, 21 and 22 showed that cells occupied distinct branches. Consistent with this, samples 20 and 21 subsequently proved to be relapsed ovarian granulosa cell tumors, known to express high levels of vimentin (Gitsch et al. (1991) Arch. Gynecol. Obstet. 249:173-177), and tumor 22 proved to be a mucinous histiotype, with the majority of cells converging on three closely related clusters expressing low levels of E-cadherin (FIG. 3A, Liu & Matulonis, supra).

The MST cell clusters were hierarchically arranged on a dendrogram based on the similarity of their protein co-expression levels in each cell cluster. In addition to subgroups of related clusters, the proteins they expressed were observed to be grouped into modules according to their co-expression patterns.

For the HG-SOC samples the three clusters with the highest median frequency of tumor cells occupied the E-cadherin branches consistent with an epithelial phenotype (FIGS. 3A and 3B, common clusters (CC) 1, 2 and 3). Protein expression patterns between the clusters showed similar (FIG. 3C left of broken line) and variable patterns (FIG. 3C right of broken line). The former may be associated with a stable and deterministic part of the transcriptome while the latter may indicate evolving stages of tumor development (McGranahan et al. (2015) Sci Transl Med. 7:283ra254). Cell surface proteins showed greater levels of variation than the intracellular pathway proteins required for tumor survival and genomic stability (Levine et al. (2015) Cell 162:184-197; Vogelstein et al. (2013) Science 339: 1546-1558).

All HG-SOC patients in this sample set were treated with a platinum-based therapeutic regimen after surgery. However, within a year, five patients from this cohort relapsed (FIG. 3A, numbers in gray font). Previous transcriptomic studies of HG-SOC samples described a mesenchymal gene expression signature that was associated with an adverse prognosis (Integrated genomic analyses of ovarian carcinoma. (2011) Nature 474:609-615; Bowtell et al., supra; Konecny et al. (2014) J. Natl. Cancer Inst 106). Consistent with these studies, mass cytometry analysis revealed that samples with a propensity to relapse contained a greater number of cells in the vimentin clade than non-relapse samples ($p=0.028$). Cells in the vimentin clade expressed significantly higher levels of cMyc and HE4 than all other cells (FIG. 4A). These findings were corroborated by hand-gating ($p=0.003$ and FIG. 4B), underscoring the accuracy of the computational findings.

The presence of previously unobserved cell subsets (EV, CC and vimentin-HE4-cMyc) that recurred across these samples strongly indicates that HG-SOC heterogeneity is not random. Therefore, presuming that relationships exist between these cell types, an alternative analysis was performed to visualize such relationships (Methods). Single cells were computationally sampled from the composite clusters and each connected on a 10-nearest-neighbor graph. This graph was subjected to a force-directed layout, placing groups of phenotypically related cells adjacently to one another. The resultant maps revealed subsets of EV cells based on their connectivity to either CC or vimentin-expressing cells. Thus, a tight connection was observed between EV1 and CC1, EV3 and EV4 with CC2, and EV5 with CC3. EV6 and EV7 were on a trajectory toward the vimentin-expressing cells. While this analysis did not establish directionality between cell types it identified distinct connections some of which may have varying capacities for tumor initiation and maintenance (Ye & Weinberg, supra; Pattabiraman et al., supra).

To further dissect the heterogeneity of the HG-SOC tumors, we computed the phenotypic diversity of all the cell clusters with Simpson's Diversity Index, used recently in a mass cytometry study of natural killer cell subtypes (Horowitz et al. (2013) Sci. Transl. Med. 5:208ra145). Here, greater heterogeneity was observed for those tumors that proceeded to relapse within a year ($p=0.0005$). Removal of cells in the vimentin clade, or all vimentin-expressing cells from the computation maintained the greater Simpson's Diversity index for the samples that proceeded to relapse (FIG. 4C). This is consistent with data from the Polyak group demonstrating that sub-clonal interactions can drive tumor growth (Marusyk et al. (2014) Nature 514:54-58; Tabassum & Polyak (2015) Nat. Rev. Cancer 15:473-483). Our data further support the existence of "structured" tumor heterogeneity which crosses a certain threshold of diversity to provide greater opportunities for groups of cells to achieve metastatic conversion. This is consistent with the higher mutational burden demonstrated in HG-SOC relapse cases (Patch et al., supra; Lawson et al., supra).

The mass cytometric studies described here enabled the phenotypic study of close to a million cells, from a relatively small set of HG-SOC samples, at an unprecedented single cell level of detail, facilitating a view of tumor heterogeneity not previously possible. The newly discovered cell subsets await genetic and functional characterization with a view to a greater understanding of their roles in tumor initiation, growth and metastasis (Marusyk et al., supra), both for HG-SOC and other epithelial tumor types.

Methods

Ovarian Cancer Cell Lines

Kuramochi and Tyk-NU cell lines (Domcke et al. (2013) Nat. Commun. 4:2126) (National Institute of Biomedical Innovation, Japanese Collection of Research Bioresources Cell Bank) and COV362 cell line (Sigma-Aldrich, Domcke et al., supra) were cultured in RPMI-1640 plus 2 mM L-glutamine (GIBCO, Invitrogen) and EMEM (American Tissue Culture Collection) respectively. Both media were supplemented with 10% heat-inactivated FBS and 100 U/ml penicillin (GIBCO, Invitrogen). The COV362 cells were cultured in DMEM (GIBCO, Invitrogen,) supplemented with 10% U/ml penicillin. Cells were split every 2-3 days and kept in a humidified cell culture incubator at 37° C. with 5% $CO_2$.

Genomic Sequencing and Analysis for BRCA1/2 and TP53

DNA was extracted and enriched through multiplex PCR (Qiagen QIAmp DNA Mini Kit and Qiagen GeneRead DNAseq Targeted Ovarian V2 Panel respectively). TrueSeq protocol was used to make an indexed Illumina sequencing library from the pooled sample amplicons. Individual sample libraries were quantitated (Qubit, Thermo) and size distribution checked (BioAnalyzer 2100, Agilent). Pooled, normalized libraries were sequenced (Illumina MiSeq). Fastq files were generated and aligned to the HG19 build of the human genome using Burrows-Wheeler aligner (Li & Durbin (2009) Bioinformatics 25:1754-1760). Gene variants were assessed using the GATK framework (McKenna et al. (2010) Genome Res 20:1297-1303). Pathogenic gene variants were identified using SnpEff (Cingolani et al. (2012) Fly (Austin) 6:80-92) and annotations in dbSNP (ncbi.nlm.nih.gov/SNP) and the IARC TP53 database (p53.iarc.fr).

Collection of Tumor Tissue

De-identified samples prepared for mass cytometry were purchased from Indivumed GmbH (Hamburg, Germany) over a two year period with a minimum of one year follow-up. Four patients were lost to follow-up. This study was conducted in compliance with the Helsinki Declaration, and all patients gave written informed consent. The use of human tissue was approved and in compliance with data protection regulations regarding the anonymization of the samples. All patients included in the study were diagnosed with ovarian cancer. Institutional review board approval was obtained at the Physicians Association in Hamburg, Germany.

Tissue Dissociation to Prepare Single Cells

Tumor tissues were collected according to Indivumed's standard operating procedures minimizing time from resection to processing. In this study time from tumor resection to freezing single cell aliquots ranged from 2 to 5 hours (median 3.5 hours). Briefly, after surgical resection, tissue samples were transferred directly to tissue transport and preservation medium DMEM/F12 supplemented with 10% fetal calf serum (FCS), 2 mM L-glutamine, 1% MEM-vitamins, 3% penicillin/streptomycin, 0.6% gentamicin (all from Pan Biotech), 5 μg/mL transferrin, 12.5 μg/mL fetuin, 20 μg/mL insulin, (all from Sigma-Aldrich) at 4-8° C. and transported to Indivumed for immediate processing. Fat and necrotic areas were removed from the tumor samples before they were chopped into small pieces for mechanical and enzymatic dissociation (GentleMACS Dissociator and human tumor dissociation kit, Miltenyi). GentleMACS programs used were: H_Tumour_1, incubate at 37° C. for 30 minutes, H_Tumour_2, incubate at 37° C. for 30 minutes, and H_Tumour_3. Resulting single cell suspensions were filtered through 100-μm and 70-μm meshes (BD Biosciences). Samples with cell viability less than 60% (determined by trypan blue staining) were not included in this study for which median cell viability was 74% (range 62-90%). Samples were then exposed to cisplatin (P4394 Sigma-Aldrich; final concentration 25 μM) for 60 seconds and the reaction quenched with RPMI/10% FBS (Fienberg et al. (2012) Cytometry A 81:467-475). After washing the cell pellet was resuspended in 5 ml Hanks buffered salt solution (HBSS) buffer with 500 μl paraformaldehyde (PFA; Electron Microscopy Sciences) (final concentration 1.6%) and incubated for 10 minutes at room temperature. Subsequently, 5 ml cell staining media (CSM; phosphate buffered saline with 0.5% bovine serum albumin, 0.02% $NaN_3$) was added and the sample was centrifuged for at 2000 rpm for 3 minutes). Supernatants were discarded and washed twice again. The cell pellets were resuspended in CSM at a density of $5 \times 10^6$ cells per 0.5 ml CSM, flash frozen and stored at −80° C.

Immunohistochemistry

Unstained slides were obtained from Indivumed. All immunohistochemistry (IHC) was performed without the use of automated immunostainers. Antigen retrieval was performed using a Decloaking Chamber (Biocare Medical) in citrate buffer at pH 6.0 at 125° C. and 15 psi. Slides were in the chamber 45 min. Incubations with primary antibodies were performed at room temperature overnight in a humidified chamber (Table 4 for information about the antibodies used). A Vectastain ABC Kit Elite and a Peroxidase Substrate Kit DAB (both from Vector Labs) were used for amplification and visualization of signal, respectively. Tissues known to contain each assessed antigen were used as positive controls. In some instances, the tissue used in the study was the best positive control. Antibody deletion controls were used for every assessed antigen to confirm specific staining.

The quantitative image analysis was based on IHC from 9 to 14 slides. The number of slides available from each sample did not permit staining with all 41 antibodies used in the mass cytometry experiment. All stained slides were scanned and digitized using the Aperio ScanScope AT Turbo to capture digital whole slide images using the 20× objective lens and stored in the Aperio Spectrum Database customized for laboratory workflow. Quantitative image analysis was performed using Spectrum version 10 and version 11, based on the FDA approved algorithms supplied by the manufacturer.

Antibodies for Mass Cytometry

Antibodies in phosphate buffered saline (PBS), without carrier protein, were conjugated to metal-chelated polymers in-house (MaxPAR antibody conjugation kit, Fluidigm) according to the manufacturer's protocol. Antibody conjugation to bismuth was carried out using a newly developed protocol (Han, G., Chen, S-Y, Gonzalez, V D, Spitzer, M, Zunder, E, Bendall, S C, Fantl, W J, Nolan, G P. Conjugation of 209Bi mass tags to antibodies enables use of the m/z=209 channel in single-cell mass cytometry. Submitted (2016)). Absorbance at 280 nm (Nanodrop 2000 spectrophotometer 2000, Thermo-Scientific) was used to dilute metal-labelled antibodies to 0.2-0.4 mg/ml in Candor PBS Antibody Stabilization solution (Candor Biosciences) for storage at 4° C. Each antibody was titrated using cell lines and primary human samples as positive and negative controls. Antibody concentrations in experiments were selected based on optimal signal to noise ratio after titrations. Labelled $^{166}$Er-CD44 and $^{89}$Y-CD45 were purchased from Fluidigm.

Sample Processing and Antibody Staining for Mass Cytometry

Single-cell suspensions of ovarian tumors and control ovarian cancer cell lines were thawed at room temperature. From each sample, 1×10$^6$ cells were aliquoted into individual tubes and were subjected to pre-permeabilisation palladium barcoding as previously reported (Behbehani et al. (2014) Cytometry A 85:1011-1019; Zunder et al. (2015) Nature Protocols 10:316-333). After barcoding, pooled cells were centrifuged and the cell pellet was then incubated for 5 minutes at room temperature with FcX block (Biolegend) to block nonspecific Fc binding. Cells were incubated with antibodies and processed for mass cytometry as previously described (Bendall et al., supra; Levine et al., supra; Gaudilliere et al. (2014) Science translational medicine 6, 255ra131; O'Gorman et al. (2015) J Allergy Clin Immunol. 136(5):1326-1336) Before loading into a CyTOF2 instrument (Fluidigm) cells were resuspended with a solution of normalization beads (Finck et al. (2013) Cytometry A 83:483-494).

Algorithms and Data Analysis

Debarcoding

Sample debarcoding was performed using a custom-written algorithm specifically adapted to the case of samples with highly varying cell sizes. The main difference from the previously published algorithm of Zunder et al. (Nature Protocols (2015) 10:316-333) was replacement of the outlier-filtering based on Mahalonobis distance with one based on z-score separation between negative and positive channels and Pearson correlation, which all are scaling-invariant measures. Invariance to vector scaling is a desirable property because cells tend to absorb different total amounts of barcoding reagents depending on their size, and we wanted to achieve equal quality of filtering for cells of all sizes. Signal intensities of each barcoding channel were first normalized by rescaling so that the 15$^{th}$ percentile became 0 and the 85$^{th}$ percentile became 1. Next, cell events were computationally filtered with a number of steps: i) cells having a sum of squares of barcoding channel value of less than 1.0 were classified as debris and removed; ii) cells having the average of the three positive barcoding channels being less than two times the average of the three negative barcoding channels were removed as doublets; iii) cells having a variance-normalized difference between three positive and three negative channels less than 2.4 were removed as doublets; iv) the remaining cells were assigned to samples based on their maximum correlation to a debarcoding key. Finally, for each sample the average of all barcoding signals was computed and then the correlation of each cell within a sample was computed to this average. The cells below the 30$^{th}$ percentile of correlation in each sample were removed. Data on remaining cells from each sample were written into separate FCS files and subject to further analysis.

Initial Assessment of Data Quality and Gating

Initial data quality was analyzed and plotted using traditional cytometry statistics and visualization methods such as histograms, dot-plots, and heat-maps with software available from Cytobank (Kotecha et al. (2010) Curr. Protoc. Cytom. Chapter 10: Unit10.17). Each data file was hand-gated to exclude debris, doublets, and dead cells that could not be distinguished by the barcodes. Tumor cells gated as CD45$^-$CD31$^-$FAP$^-$ were used for further computationally driven analysis.

Clustering

The raw CyTOF data was subject to ar sin h(x/5) transformation. Cells from each sample were selected and then pooled together for clustering, resulting in a dataset of a total of 806,314 cells. This dataset was clustered with a novel density-based clustering method termed X-shift (Samusik et al., supra). X-shift was developed to compute large multidimensional datasets and to automatically select the optimal number of clusters. Briefly, X-shift uses the weighted K-nearest neighbor density estimation to find the local maxima of data-point (cell event) density in multidimensional marker space. X-shift computes the density estimate for each data point and then searches for the local density maxima in a nearest-neighbor graph, which become cluster centroids. All the remaining data points are then connected to the centroids via density-ascending paths in the graph, thus forming clusters. Finally, the algorithm checks for the presence of density minima on a straight line segment between the neighboring centroids and merges the clusters as necessary. Clusters separated by a Mahalonobis distance less than 2.0 were merged. The optimal nearest neighbor parameter, K, was selected to be 35 in a data-driven manner, by finding the elbow-point of the plot of number of clusters over K. All data processing was performed with the VorteX clustering environment (stanford.edu/~samusik/vortex).

Statistical Analysis

All statistical analyses were performed in Microsoft Excel.

Ordering Markers by their Expression Variability in the Common Clusters (CC)

In FIG. 3, the phenotypic and signaling markers are shown in descending order determined by the ratio of standard deviations (SDs) within the CCs to the SD of a given parameter within all clusters.

t-tests

One-tailed Student's t-tests (uneven sample size, uneven variance) were performed on ranked transformed values due to non-normal distribution of the data. Tests were performed on ten non-relapse HG-SOC samples and five that proceeded to relapse within one year. Four HG-SOC samples were excluded from the analysis due to unavailable follow-up information. Three samples were non-HG-SOC.

Dendrograms

Dendrograms were generated using hierarchical agglomerative clustering implemented in the VorteX clustering environment (stanford.edu/~samusik/vortex).

Minimum Spanning Trees

Minimum spanning trees were generated by creating a complete graph where cell populations were represented as nodes and edge weights were given by the angular distance between the median marker expression vectors, and consecutively applying the standard reverse-delete algorithm on that graph. Layout and visualization were performed using Gephi Toolkit 0.8.7 library.

Single Cell Force-directed Layout

Cells events were selected randomly from each composite cluster, where the number of events taken was given by the formula $$n = 50 \cdot \sqrt[3]{\text{cluster\_size}}.$$

Cell events were placed as nodes in a graph and connected with unweighted edges to 10 nearest neighbors in the phenotypic space (angular distance). The resulting graph was subject to a force-directed layout using the ForceAtlas2 algorithm (Jacomy et al. (2014) PLoS One 9:e98679). Layout and visualization were produced using Gephi-Toolkit v0.8.7 (gephi.org/toolkit/).

Simpson's Index of Diversity

The Simpson's index of diversity of the j-th tumor sample was computed as $$1 - \sum_{i=1}^{k} \left(\frac{n_{ij}}{N_j}\right)^2,$$

which sums each i-th cluster, where i lies between 1 and k with k being the total number of clusters. $n_{ij}$ is the number of cells in the i-th cluster that belong to the j-th sample, and $N_j$ is a total number of cells in the j-th sample.

TABLE 1

Clinical characteristics of patient samples.

| Case no | Patient ID | Age at case start (yr) | Weight (kg) | Body mass index | Description | Localization | Histological type | Stage | Radicality | Grade | Morphology | MUC16/CA-125 (U/ml) |
|---|---|---|---|---|---|---|---|---|---|---|---|---|
| 1 | X2617 | 63 | 79.0 | 29.0 | malignant neoplasm of ovary | ovary | ovarian carcinoma - serous type | III C | R2 | G3 | serous cystadenocarcinoma, NOS | 2418.7 |
| 2 | X2619 | 57 | 100.0 | 35.4 | malignant neoplasm of ovary | ovary | ovarian carcinoma - serous type | IIC | R0 | G2 | serous cystadenocarcinoma, NOS | n/a |
| 3 | R866 | 60 | 89.0 | 31.5 | malignant neoplasm of ovary | ovary | ovarian carcinoma - serous papillary type | IA | R0 | G1 | papillary serous cystadenocarcinoma | n/a |
| 4 | R873 | 63 | 84.0 | 30.9 | malignant neoplasm of ovary | ovary | ovarian carcinoma - mucinous adenocarcinoma | IA | R0 | G2 | mucinous adenocarcinoma | 36.2 |
| 5 | Z289 | 79 | 65.0 | 25.4 | malignant neoplasm of ovary | ovary | ovarian carcinoma - serous papillary type | III C | n/a | G3 | papillary serous cystadenocarcinoma | 355.5 |
| 6 | X2648* | 67 | 78 | 27 | malignant neoplasm of ovary | peritoneum | ovarian carcinoma - serous papillary type | III C | R1 | G3 | serous cystadenocarcinoma, NOS (C56.9) | 461 |
| 7 | Z378 | 71 | 77.0 | 26.6 | malignant neoplasm of ovary | ovary | ovarian carcinoma - serous papillary type | III C | R0 | G3 | serous cystadenocarcinoma, NOS (C56.9) | 44.4 |
| 8 | X2643 | 53 | 77.0 | 24.3 | malignant neoplasm of ovary | peritoneum | ovarian carcinoma - serous papillary type | III B | R0 | G3 | serous cystadenocarcinoma, NOS (C56.9) | 614.2 |
| 9 | Z393 | 69 | 63.0 | 22.9 | malignant neoplasm of ovary | ovary | ovarian carcinoma | n/a | R0 | n/a | granulosa cell tumor, malignant (C56.9) | 8.6 |
| 10 | Z403 | 82 | 71.0 | 27.1 | malignant neoplasm of ovary | ovary | ovarian carcinoma | III C | n/a | G3 | serous surface papillary carcinoma (C56.9) | 129.7 |
| 11 | X2638 | 72 | 80.0 | 32.0 | malignant neoplasm of ovary | ovary | adenocarcinoma | IV | R2 | n/a | adenocarcinoma, NOS | 318 |
| 12 | Z367* | 64 | 65.0 | 20.5 | malignant neoplasm of ovary | ovary | ovarian carcinoma - serous papillary type | III C | RX | G1 | serous cystadenocarcinoma, NOS | 267.7 |

TABLE 1-continued

Clinical characteristics of patient samples.

| Case no | Patient ID | Age at case start (yr) | Weight (kg) | Body mass index | Description | Localization | Histological type | Stage | Radicality | Grade | Morphology | MUC16/CA-125 (U/ml) |
|---|---|---|---|---|---|---|---|---|---|---|---|---|
| 13 | Z377† | 56 | 108.0 | 35.7 | malignant neoplasm of ovary | ovary | ovarian carcinoma - serous papillary type | IV | R0 | G1 | serous surface papillary carcinoma | 541.5 |
| 14 | Z467 | 48 | 72 | 24.3 | malignant neoplasm of ovary | omentum | ovarian carcinoma - serous papillary type | III C | R0 | G3 | serous cystadenocarcinoma, NOS (C56.9) | 135.1 |
| 15 | R1116 | 67 | 72 | 27.4 | malignant neoplasm of ovary | ovary | ovarian carcinoma - serous papillary type | III C | R1 | G3 | serous surface papillary carcinoma (C56.9) | 481.6 |
| 16 | R1118 | 84 | 53 | 19.2 | malignant neoplasm of ovary | ovary | ovarian carcinoma - serous type | III A | RX | G3 | serous cystadenocarcinoma, NOS (C56.9) | 360.3 |
| 17 | Z500 | 58 | 85 | 30.1 | malignant neoplasm of ovary | ovary | ovarian carcinoma - serous papillary type | III C | R0 | G3 | serous surface papillary carcinoma (C56.9) | n/a |
| 18 | X2661* | 74 | 63 | 24.6 | malignant neoplasm of ovary | peritoneum | ovarian carcinoma - serous papillary type | III C | R2 | G3 | serous surface papillary carcinoma (C56.9) | 813.5 |
| 19 | R1153 | 88 | 47 | 19.6 | malignant neoplasm of ovary | ovary | ovarian carcinoma - serous papillary type | III C | R2 | n/a | papillary serous cystadenocarcinoma (C56.9) | 90.4 |
| 20 | R1156 | 46 | 83 | 28.1 | malignant neoplasm of ovary | peritoneum | ovarian carcinoma | IIB | R0 | n/a | granulosa cell tumor, malignant (C56.9) | 3.9 |
| 21 | Z536 | 82 | 56 | 19.8 | malignant neoplasm of ovary | omentum | ovarian carcinoma - serous papillary type | III C | RX | G3 | serous cystadenocarcinoma, NOS (C56.9) | 1124 |
| 22 | X2667 | 69 | 61 | 22.4 | malignant neoplasm of ovary | ovary | ovarian carcinoma - serous papillary type | III C | R0 | G3 | serous surface papillary carcinoma (C56.9) | 159.1 |

Chemo-naive tumors used in this study were all diagnosed as malignant neoplasms of the ovary. Most were late stage and all patients underwent surgical de-bulking followed by a platinum-based chemotherapeutic regimen.
Clinical follow-up information was unavailable for patients X2648, X2661 and Z367 (*) and patient Z377 died during surgery (†).

TABLE 2

Pathogenic variants of TP53.

| Sample | Chrom | Pos | rs ID | REF | ALT | Consequence | COSMIC DB | Clinvar DB |
|---|---|---|---|---|---|---|---|---|
| FF-R1118 | chr17 | 7577548 | rs28934575 | C | A | MV | COSM10957 | pathogenic |
| FF-X2648 | chr17 | 7577593 | NA | TAC | T | FV:FT | COSM111635 | NA |
| FF-Z367 | . | . | . | . | . | . | . | . |
| VF-X2617 | . | . | . | . | . | . | . | . |
| VF-X2619 | chr17 | 7577539 | rs121912651 | G | A | MV | COSM10656 | pathogenic |
| FF-X2643 | chr17 | 7577082 | NA | C | T | MV | COSM10726 | NA |
| FF-Z377 | chr17 | 7578403 | NA | C | T | MV | COSM10645 | NA |
| FF-Z403 | chr17 | 7578394 | NA | T | A | MV | COSM10889 | NA |
| VF-Z500 | chr17 | 7578190 | rs121912666 | T | C | MV | COSM10758 | pathogenic |
| VF-Z536 | chr17 | 7577538 | rs11540652 | C | T | MV | COSM10662 | pathogenic |
| FF-X2661 | chr17 | 7579358 | rs11540654 | C | G | MV | COSM10716 | NA |
| VF-R866 | chr17 | 7578435 | NA | C | CAG | FV:FT | NA | NA |
| VF-Z289 | chr17 | 7577539 | rs121912651 | G | A | MV | COSM10656 | pathogenic |
| VF-Z467 | . | . | . | . | . | . | . | . |
| FF-X2638 | chr17 | 7577520 | NA | A | C | MV | COSM1230106 | NA |
| FF-Z378 | chr17 | 7578290 | NA | C | T | SAV | COSM127200 | NA |
| FF-R1156 | . | . | . | . | . | . | . | . |
| FF-Z393 | . | . | . | . | . | . | . | . |
| VF-R873 | . | . | . | . | . | . | . | . |

| Sample | Zygosity | aa cDNA | SIFT prediction | IARC SC | HG-SOC Group | TP53WT |
|---|---|---|---|---|---|---|
| FF-R1118 | 0.96 | p.G245R | deleterious | 19 | HG-NG | no |
| FF-X2648 | 0.333 | p.C229fs*10 | NA | NA | HG-NG | no |
| FF-Z367 | . | . | . | . | HG-NG | yes |
| VF-X2617 | . | . | . | . | HG-NG | yes |
| VF-X2619 | 0.818 | p.R248W | deleterious | 734 | HG-NG | no |
| FF-X2643 | 0.659 | p.E286K | deleterious | 96 | HG-SOC1 | no |
| FF-Z377 | 0.255 | p.C176F | deleterious | 164 | HG-SOC1 | no |
| FF-Z403 | 0.741 | p.H179R | deleterious | 172 | HG-SOC1 | no |
| VF-Z500 | 0.785 | p.Y220C | deleterious | 396 | HG-SOC1 | no |
| VF-Z536 | 0.816 | p.R248Q | deleterious | 993 | HG-SOC1 | no |
| FF-X2661 | 0.674 | p.R110L | deleterious | 36 | HG-SOC2 | no |
| VF-R866 | 0.375 | . | NA | NA | HG-SOC2 | no |
| VF-Z289 | 0.286 | p.R248W | deleterious | 734 | HG-SOC2 | no |
| VF-Z467 | . | . | . | . | HG-SOC2 | yes |
| FF-X2638 | 0.826 | p.I254S | deleterious | 7 | HG-SOC3 | no |
| FF-Z378 | 0.622 | c.560-1G > T | NA | NA | HG-SOC3 | no |
| FF-R1156 | . | . | . | . | non-HGSOC | yes |
| FF-Z393 | . | . | . | . | non-HGSOC | yes |
| VF-R873 | . | . | . | . | non-HGSOC | yes |

Pathogenic deleterious TP53 variants identified by targeted exome sequencing were present in 13/16 (81%) HG-SOC samples.
NG—non-grouped,
SC—somatic count,
MV—missense variant,
FV—frameshift variant,
SAV—Splice acceptor variant,
FT—feature truncation,
FE—feature elongation.
Samples that proceeded to relapse in gray font. Sequencing was performed on fixed frozen (FF) or viably frozen (VF) sample depending on sample availability. Material was unavailable for samples X2667, R1116 and R1153.
Rows of dots indicate no pathogenic variant was identified. Sequencing of BRCA1 and BRCA2 coding regions did not identify validated pathogenic variants (not shown).

TABLE 3

Antibodies used in this study.

| Isotope | Antigen | Clone | Phosphorylation site | Vendor | Positive control cell line | Negative control cell line |
|---|---|---|---|---|---|---|
| Y 89 | CD45 | H130 | | DVS | U937 | OVCAR3 |
| In 113 | FAP | F11-24 | | eBioscience | WI-38 | Ramos |
| In 115 | Vimentin | D21H3 | | CST | NIH3T3 | OVCAR3 |
| Ce 140 | CD31 | WM59 | | Biolegend | HUVEC | U937 |
| Pr 141 | CD73 | AD2 | | BD | HUVEC | Ramos |
| Nd 142 | CD61 | VI-PL2 | | BD | PBMC - Monocytes | PBMC - CD3+ |
| Nd 143 | CA125 | X75 (3C8/4) | | Gen Way | OVCAR3 | U937 |
| Nd 144 | CD90 | 5E10 | | Biolegend | OVKATE | U937 |
| Nd 145 | CD151 | 50-6 | | Biolegend | OVCAR4 | Ramos |
| Nd 146 | pATM | 10H11.E12 | pS1981 | Millipore | U937 - Etoposide 6 hr | U937 - Unstim (vehicle control) |
| Sm 147 | pH2AX | JBW301 | pS139 | Millipore | U937 - Etoposide 6 hr | U937 - Unstim (vehicle control) |
| Nd 148 | Cyclin B1 (total) | GNS-1 | | BD | HCT116 - Nocodazole 18 h | HCT116 - Unstim (vehicle control) |
| Sm 149 | pNFkB | K10-895.12.50 | pS529 | BD | Jurkat, TNFa 15 min | Jurkat - Unstim (vehicle control) |
| Nd 150 | pBcl2 | 5H2 | pS70 | CST | OVCAR3 - Paclitaxel 24 hr | OVCAR3 - Unstim (vehicle control) |
| Eu 151 | pERK | D13.14.4E | pT202/pY204 | CST | Jurkat - Pervanadate 15 min | Jurkat - Unstim (vehicle control) |
| Sm 152 | Ki67 (total) | B56 | | BD | OVCAR4 | OVKATE |
| Eu 153 | CD49f | MP4F10 | | R&D system | CaCo | Ramos |
| Sm 154 | pSTAT3 | 4/P-STAT3 | pY705 | BD | Jurkat - Pervanadate 15 min | Jurkat - Unstim (vehicle control) |
| Gd 155 | CD133 | AC133 | | Miltenyi | CaCo | Ramos |
| Gd 156 | CD10 | HI10a | | Biolegend | REH | U937 |
| Gd 157 | Snail1 | 20C8 | | eBiosciences | HCT116 | PBMC |
| Gd 158 | E-Cadherin | 67A4 | | Biolegend | OVCAR3 | U937 |
| Tb 159 | pAkt | D9E | pS473 | CST | Kuramochi, serum starved O/N, EGF 10 min | Kuramochi - serum starved O/N, vehicle control |
| Gd 160 | Sox2 | O30-678 | | BD | OVCAR3 | U937 |
| Dy 161 | c-Myc | D84C12 | | CST | TykNu | MCF7 |
| Dy 162 | pSTAT5 | 47/Stat5 | pY694 | BD | Jurkat - Pervanadate 15 min | Jurkat - Unstim (vehicle control) |
| Dy 163 | Endoglin | 43A3 | | Biolegend | HELA | U937 |
| Dy 164 | CD24 | ML5 | | Biolegend | Kuramochi | U937 |
| Ho 165 | pRb | J112-906 | pS807/pS811 | BD | OVSAHO | PBMC |
| Er 166 | 0D44 | BJ18 | | DVS | COV362 | OVCAR3 |
| Er 167 | PAX8 | polyclonal | | ProteinTech | Kuramochi | U937 |
| Er 168 | CD13 | L138 | | BD | TykNu-Pt res. | OVCAR4 |
| Tm 169 | HE4 | EPR4743 | | Abcam | Kuramochi | U937 |
| Er 170 | Non-phospho-β-Catenin | D13A1 | | CST | Kuramochi | U937 |
| Yb 171 | cPARP | F21-852 | cleaved N214 | BD | U937 - Etoposide 24 hr | U937 - Unstim (vehicle control) |
| Yb 172 | prpS6 | N7-548 | pS235/pS236 | BD | OVCAR4 | U937 |
| Yb 173 | Mesothelin | MB-G10 | | Rockland | Kuramochi | U937 |

TABLE 3-continued

Antibodies used in this study.

| Isotope | Antigen | Clone | Phosphorylation site | Vendor | Positive control cell line | Negative control cell line |
|---|---|---|---|---|---|---|
| Yb 174 | pCREB | 87G3 | pS133 | CST | U937 -PMA 10 min | U937 - Unstim (vehicle control) |
| Lu 175 | Total p53 | 1C12 | | CST | Kuramochi | U937 |
| Yb 176 | pHH3 | HTA28 | pS28 | Biolegend | HCT116 - Nocodazole 18 h | HCT116 - Unstim (vehicle control) |
| Bi 209 | ROR1 | 4A5 | | gift from Prof. T. Kipps | Jeko | Jurkat |

Antibody clones were selected based on their performance in fluorescence-based flow cytometry and all, except for $^{89}$Y-CD45 and $^{166}$Er-CD44, were conjugated in-house. Working concentrations were optimized by titration against positive and negative cell lines as shown (right-hand columns).

TABLE 4

Antibodies used for IHC.

| Antigen | Antibody Source (clone) | Vendor | Catalog Number | Dilution |
|---|---|---|---|---|
| Vimentin | Rb mAb (D21h3) | Cell Signaling Technologies | 5741S | 1:800 |
| cPARP | Rb mAb (D64E10) | Cell Signaling Technologies | 5625S | 1:100 |
| E-Cadherin | Rb mAb (24E10) | Cell Signaling Technologies | 31957 | 1:1000 |
| pAkt (S473) | Rb mAb (D9E) | Cell Signaling Technologies | 4060 | 1:1600 |
| CD45 | Rb mAb (EP322Y) | Novus | NB110-55702 | 1:250 |
| cCaspase-3 | Rb pAb | Promega | G7481 | 1:1000 |
| p53 | Rb pAb | Santa Cruz | sc-6243 | 1:1000 |
| FAP | Rb pAb | Abcam | ab110779 | 1:500 |
| CD31 | Goat pAb | Santa Cruz | sc-1506 | 1:1600 |
| pErk(T202/Y204) | Rb mAb | Cell Signaling Technologies | 4370 | 1:500 | mAb—monoclonal antibody, pAb—polyclonal antibody, Rb—rabbit

EXAMPLE 2

Identification of a Single Cell Subset in Primary Ovarian Cancer as a Predictor of Relapse Introduction Here we report a specific tumor cell subset that is predictive of time from diagnosis to relapse for ovarian cancer. The identity of these cells was enabled by single-cell high dimensional mass cytometry as described in Example 1. These data can be adapted to a three-color flow cytometry, immunohistochemistry or immunofluorescence test.

Results

Single-cell analysis of diagnostic chemotherapy-primary HG-SOC specimens produced the following observations: Samples were analyzed using a clustering algorithm that grouped cells together with similarity of their maker co-expression patterns in high dimensions. Data from points 2 to 11 is from the clustering analysis and from points 12 to X is based on hand-gating, the gold standard for analysis of flow cytometry data. The bulk of cells in each tumor expressed E-cadherin, a hallmark of the epithelial phenotype. A small number of cell subsets were devoid of E-cadherin but expressed vimentin, a hallmark of the mesenchymal phenotype associated with invasion and metastasis. A small number of cells co-expressed both E-cadherin and vimentin suggesting these cells were undergoing epithelial-to-mesenchymal transition (EMT). The cells undergoing EMT were rich in their co-expression of stem cell markers. The cells undergoing EMT were rich in their co-expression of transcription factors. Within HG-SOC samples there were distinct groupings of samples based on relative frequency of specific cell types. Specifically, there were three commonly occurring clusters each one distinguishing a group of HG-SOC tumor samples. Dispersed across the tumor groups were samples from patients that subsequently underwent relapse. The relapse samples (here defined as less than 1 year) had an increased frequency of vimentin-expressing cells compared to the non-relapse samples (p-value 0.018). When compared to all the other cells in the data-set, the vimentin-expressing cells that distinguished relapse from non-relapse samples were devoid of E-cadherin and expressed elevated levels of cMyc and HE4. The computational analysis was complemented with hand-gating, a well-accepted and gold-standard tool for analyzing flow cytometry data. Vimentin-expressing cells were gated out of i) the entire tumor-cell compartment and ii) the E-cadherin negative cells in the tumor compartment. Note that tumors comprise other cells types such as immune, stromal and angiogenic cells. Markers were included to remove those cells from the analysis. Within the tumor-cell compartment, there was an increase in frequency of cells that were double positive for cMyc and vimentin in the relapse compared to the non-relapse samples (FIG. 5B). Within the tumor-cell compartment there was an increased frequency of cells that were double positive for cMyc and HE4 in the relapse compared to the non-relapse samples (FIG. 5C). Within the tumor-cell compartment there was an increased frequency of cells that were double positive for HE4 and vimentin in the relapse compared to the non-relapse samples (FIG. 5A). Within the E-cadherin negative population of the tumor-cell compartment there was an increased frequency of cells that were double positive for cMyc and vimentin in the relapse compared to the non-relapse samples (FIG. 5B). Within the E-cadherin negative population of the tumor-cell compartment that was E-cadherin negative there was an increased frequency of cells that were double positive for cMyc and HE4 in the relapse compared to the non-relapse samples (FIG. 5C). Within the E-cadherin negative population of the tumor-cell compartment, there was an increased frequency of cells that were double positive for cMyc and vimentin in the relapse compared to the non-relapse samples (FIG. 5B).

Log-rank analysis revealed that HG-SOC patients with tumors having greater than 1% cMyc/HE4 cells were 13 times more likely to undergo relapse than those patients with tumors harboring less than 1% of those cells (FIG. 6). A Cox-proportional hazard analysis showed minimal impact of age, body mass index (BMI), weight or blood CA125 levels.

Applications

Thus, we have provided a new test with which to more reliably predict time to relapse for ovarian cancer patients. The frequency of cells within a diagnostic chemotherapy-primary HG-SOC specimen expressing vimentin, cMyc and HE4 can be measured to evaluate time from diagnosis to relapse. The frequency of cells within a diagnostic chemotherapy-primary HG-SOC specimen that are negative for E-cadherin and positive for cMyc, vimentin and HE4, or any combination thereof, can be measured, for example, by mass cytometry, fluorescent flow cytometry, immunohistochemistry, immunofluorescence, or multiplexed ion beam imaging (MIBI). Alternatively, single cell mRNA levels of vimentin, cMyc and HE4 coding transcripts can be measured to determine time from diagnosis to relapse. The ability to detect a subset of cells predictive of relapse should improve clinical management of ovarian cancer and also be useful for monitoring therapeutic responses of ovarian cancer patients to treatment.

While the preferred embodiments of the invention have been illustrated and described, it will be appreciated that various changes can be made therein without departing from the spirit and scope of the invention.

What is claimed is:

1. A prognostic method for predicting relapse of an ovarian cancer patient and treating the patient for ovarian cancer, the method comprising:
   a) obtaining a sample of ovarian tumor tissue from the patient, wherein the ovarian tumor tissue comprises a heterogeneous population of tumor cells;
   b) measuring frequency of tumor cells coexpressing at least two markers selected from the group consisting of vimentin, cMyc and HE4 in the sample of the ovarian tumor tissue; and
   c) comparing the frequency of the tumor cells expressing said markers in the sample of ovarian tumor tissue to respective reference value ranges for tumor cells coexpressing said at least two markers for ovarian cancer patients who do not relapse, wherein increased frequency of tumor cells positive for both vimentin and HE4, tumor cells positive for both vimentin and cMyc, tumor cells positive for both HE4 and cMyc, or tumor cells positive for all three of the markers, vimentin, HE4, and cMyc, compared to the reference value ranges of the tumor cells positive for said at least two markers for ovarian cancer patients who do not relapse indicates the patient will relapse within 1 year; and
   d) treating the patient with surgery, radiation therapy, chemotherapy, targeted therapy, anti-angiogenic therapy, or immunotherapy, or any combination thereof, if the patient is predicted to relapse.

2. The method of claim 1, wherein a frequency of the tumor cells positive for both vimentin and HE4, the tumor cells positive for both vimentin and cMyc, the tumor cells positive for both HE4 and cMyc, or the tumor cells positive for all three of the markers, vimentin, HE4, and cMyc, greater than 1% indicates increased likelihood that the ovarian cancer patient will relapse.

3. The method of claim 1, wherein increased frequency of the tumor cells positive for vimentin that also have higher levels of expression of cMyc and HE4 compared to the reference value ranges for ovarian cancer patients who do not relapse indicates increased likelihood that the ovarian cancer patient will relapse.

4. The method of claim 1, further comprising detecting whether the tumor cells having increased frequency of the at least two markers selected from the group consisting of vimentin, cMyc and HE4 are E-cadherin negative cells, wherein absence of the E-cadherin in the tumor cells indicates increased likelihood that the ovarian cancer patient will relapse compared to if the tumor cells are E-cadherin positive.

5. The method of claim 1, wherein the ovarian cancer is high-grade serous ovarian cancer.

6. The method of claim 1, wherein said measuring the frequency of the tumor cells comprises performing multi-parametric single cell analysis.

7. The method of claim 1, wherein the markers are detected using mass cytometry, flow cytometry, immunohistochemistry, immunofluorescence, multiplexed ion beam imaging (MIBI), or other multi-parametric single cell analysis technology.

8. The method of claim 1, wherein said measuring the frequency of the tumor cells comprises detecting said at least two markers using an antibody that specifically binds to vimentin, cMyc or HE4, or a fragment thereof containing an antigenic determinant of vimentin, cMyc or HE4.

9. The method of claim 8, wherein the antibody is selected from the group consisting of a monoclonal antibody, a polyclonal antibody, a chimeric antibody, a recombinant fragment of an antibody, an Fab fragment, an Fab' fragment, an F(ab')$_2$ fragment, an F$_v$, fragment, and an scF$_v$, fragment.

10. The method of claim 8, wherein the antibody is conjugated to a detectable label.

11. The method of claim 10, wherein the detectable label is a stable-metal isotope or a fluorescent label.

12. The method of claim 1, wherein the surgery comprises a unilateral oophorectomy, a bilateral oophorectomy, or a salpingo oophorectomy.

13. The method of claim 1, wherein the patient is human.

14. The method of claim 1, further comprising measuring numbers of the tumor cells positive for all three of the markers, vimentin, HE4, and cMyc, wherein increased numbers of the tumor cells positive for all three of the markers, vimentin, HE4, and cMyc, compared to reference value ranges for ovarian cancer patients who do not relapse indicates an increased likelihood that the ovarian cancer patient will relapse.

15. The method of claim 1, further comprising measuring levels of HE4 and cMyc in the tumor cells positive for vimentin, wherein increased levels of HE4 and cMyc in the tumor cells positive for vimentin compared to reference value ranges for ovarian cancer patients who do not relapse indicates an increased likelihood that the ovarian cancer patient will relapse.

* * * * *